(12) United States Patent
Kohrman et al.

(10) Patent No.: US 11,998,777 B2
(45) Date of Patent: Jun. 4, 2024

(54) SERVICEABLE RESPIRATOR SYSTEM WITH CONFIGURABLE COMPONENTS

(71) Applicant: Auburn University, Auburn, AL (US)

(72) Inventors: Zachary Eugene Hubert Kohrman, Bay Minette, AL (US); Michael John Kohrman, Bay Minette, AL (US)

(73) Assignee: Auburn University, Auburn, AL (US)

( * ) Notice: Subject to any disclaimer, the term of this patent is extended or adjusted under 35 U.S.C. 154(b) by 193 days.

(21) Appl. No.: 17/385,736

(22) Filed: Jul. 26, 2021

(65) Prior Publication Data

US 2022/0023674 A1 Jan. 27, 2022

Related U.S. Application Data

(60) Provisional application No. 63/215,562, filed on Jun. 28, 2021, provisional application No. 63/057,482, (Continued)

(51) Int. Cl.
*A62B 7/10* (2006.01)
*A41D 13/11* (2006.01)
(Continued)

(52) U.S. Cl.
CPC ............ *A62B 7/10* (2013.01); *A41D 13/1161* (2013.01); *A61F 9/029* (2013.01);
(Continued)

(58) Field of Classification Search
CPC .... A62B 7/10; A62B 7/02; A62B 7/04; A62B 7/12; A62B 7/14; A62B 9/02; A62B 9/04;
(Continued)

(56) References Cited

U.S. PATENT DOCUMENTS 4,648,394 A 3/1987 Wise
5,592,935 A 1/1997 Elstran et al.
(Continued)

FOREIGN PATENT DOCUMENTS

EP 2165739 3/2010
KR 101649715 B1 8/2016

OTHER PUBLICATIONS

European Patent Office, International Search Report for International Application No. PCT/US2021/043174, dated Sep. 24, 2021.
(Continued)

*Primary Examiner* — Joseph D. Boecker
*Assistant Examiner* — Brian T Khong
(74) *Attorney, Agent, or Firm* — Jacob W Neu; Bradley Arant Boult Cummings, LLP

(57) ABSTRACT

There is provided a respirator for supplying clean air for a wearer. The respirator comprises a face assembly comprising an oronasal mask configured to seal against and cover a nose region and a mouth region of the wearer. The face assembly may be configured to be interchangeable on the respirator between a half-face assembly and a full-face assembly. The respirator comprises a securing headgear releasably securable with the face assembly, the securing headgear assembly configured to secure the respirator on a head of the wearer. The respirator comprises a facepiece assembly for supplying the wearer with air for inhaling and releasing air exhaled by the wear, the facepiece assembly releasably securable with the face assembly. One or more of the face assembly, the facepiece assembly, or the securing headgear are configured to be released from the respirator, sterilized, and releasably resecured with the respirator.

18 Claims, 29 Drawing Sheets

Related U.S. Application Data filed on Jul. 28, 2020, provisional application No. 63/057,143, filed on Jul. 27, 2020.

(51) Int. Cl.

| | |
|---|---|
| *A61F 9/02* | (2006.01) |
| *A61M 16/06* | (2006.01) |
| *A61M 16/10* | (2006.01) |
| *A62B 9/02* | (2006.01) |
| *A62B 19/00* | (2006.01) |

(52) U.S. Cl.
CPC ...... *A61M 16/0627* (2014.02); *A61M 16/105* (2013.01); *A62B 9/02* (2013.01); *A62B 19/00* (2013.01)

(58) Field of Classification Search
CPC ....... A62B 19/00; A62B 18/006; A62B 18/02; A62B 18/025; A62B 18/04; A62B 18/045; A62B 18/08; A62B 18/084; A62B 18/10; A62B 23/02; A61M 16/0627; A61M 16/06; A61M 16/0605; A61M 16/0611; A61M 16/0616; A61M 16/0622; A61M 16/105; A41D 13/1161; A41D 13/1184; A41D 13/1153; A41D 13/11; A61F 9/029; A61F 9/028; A61F 9/025; A61F 9/026; A61F 9/027
See application file for complete search history.

(56) References Cited

U.S. PATENT DOCUMENTS

| | | | |
|---|---|---|---|
| 5,662,142 A | 9/1997 | Ansite | |
| 5,924,420 A | 7/1999 | Reischel et al. | |
| 6,062,221 A | 5/2000 | Brostrom et al. | |
| 6,099,097 A | 8/2000 | Hocker et al. | |
| 6,584,976 B2 | 7/2003 | Japuntich et al. | |
| 6,626,178 B2 | 9/2003 | Morgan et al. | |
| 6,732,733 B1 | 5/2004 | Brostrom et al. | |
| 6,805,124 B2 | 10/2004 | Japuntich et al. | |
| 6,817,362 B2 | 11/2004 | Gelinas et al. | |
| 6,823,865 B2 | 11/2004 | Drew et al. | |
| 6,874,499 B2 | 4/2005 | Viner et al. | |
| 6,883,518 B2 | 4/2005 | Mittelstadt et al. | |
| 7,013,891 B2 | 3/2006 | Richardson et al. | |
| 7,013,895 B2 | 3/2006 | Martin et al. | |
| 7,188,622 B2 | 3/2007 | Martin et al. | |
| 7,243,676 B2 | 6/2007 | Bailey | |
| 7,448,376 B2 | 11/2008 | Lepel | |
| 7,594,508 B2 | 9/2009 | Doyle | |
| 8,783,252 B2 | 7/2014 | Pierro et al. | |
| 8,882,703 B2 | 11/2014 | Hickle | |
| 8,925,548 B2 | 1/2015 | Pierro et al. | |
| 8,944,059 B2 | 2/2015 | Mansour et al. | |
| 8,944,060 B2 | 2/2015 | Varga et al. | |
| 9,044,562 B2 | 6/2015 | Dillingham et al. | |
| 9,126,004 B2 | 9/2015 | Flynn, Sr. | |
| 9,248,248 B2 | 2/2016 | Virr et al. | |
| 9,468,782 B2 | 10/2016 | Koehler | |
| 9,517,367 B2 | 12/2016 | Dwyer et al. | |
| 9,725,178 B2 | 8/2017 | Wang | |
| 9,744,493 B2 | 8/2017 | Legare et al. | |
| 9,833,644 B2 | 12/2017 | Hansel et al. | |
| 10,166,417 B2 | 1/2019 | Sutton et al. | |
| 10,525,292 B2 | 1/2020 | Tang et al. | |
| 10,661,104 B2 | 5/2020 | Morgan et al. | |
| 10,786,691 B2 | 9/2020 | Kao et al. | |
| 2004/0261795 A1 | 12/2004 | Brunell | |
| 2006/0201511 A1* | 9/2006 | Freriks | A62B 17/04 128/206.13 |
| 2008/0210242 A1 | 9/2008 | Burk et al. | |
| 2011/0056496 A1* | 3/2011 | Tilley | A62B 9/04 128/205.27 |
| 2012/0160245 A1 | 6/2012 | Leuschner et al. | |
| 2014/0261431 A1 | 9/2014 | Murphy | |
| 2015/0202473 A1 | 7/2015 | Curran et al. | |
| 2016/0001111 A1* | 1/2016 | Morgan | A62B 18/082 128/205.12 |
| 2016/0059049 A1* | 3/2016 | Langford | A61M 16/06 128/205.27 |
| 2017/0021201 A1 | 1/2017 | Baker et al. | |
| 2017/0021203 A1* | 1/2017 | Baker | A62B 7/12 |
| 2017/0050057 A1* | 2/2017 | Sabolis | A62B 23/02 |
| 2019/0209804 A1 | 7/2019 | Dantanarayana et al. | |

OTHER PUBLICATIONS

European Patent Office, Written Opinion of the International Searching Authority for International Application No. PCT/US2021/043174, dated Sep. 24, 2021.

* cited by examiner

DETAIL A

DETAIL B

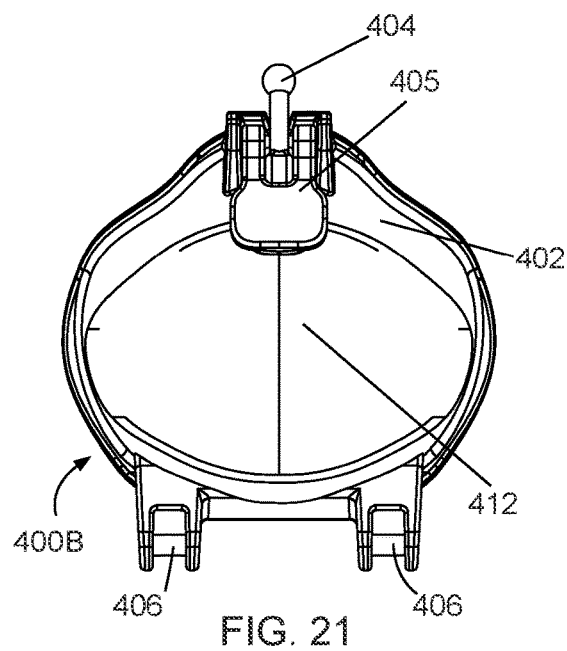
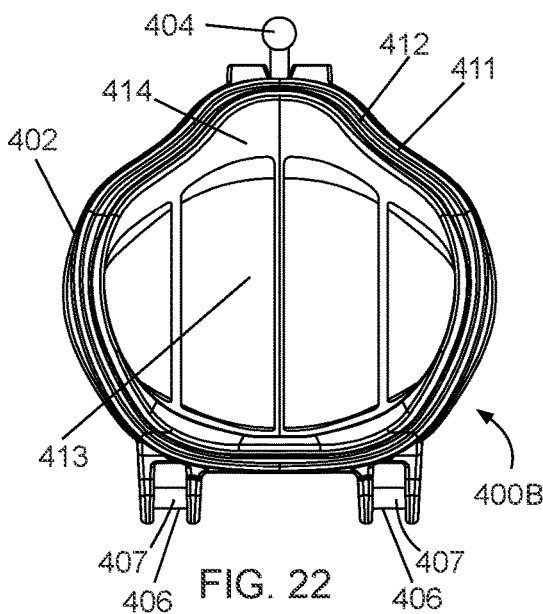
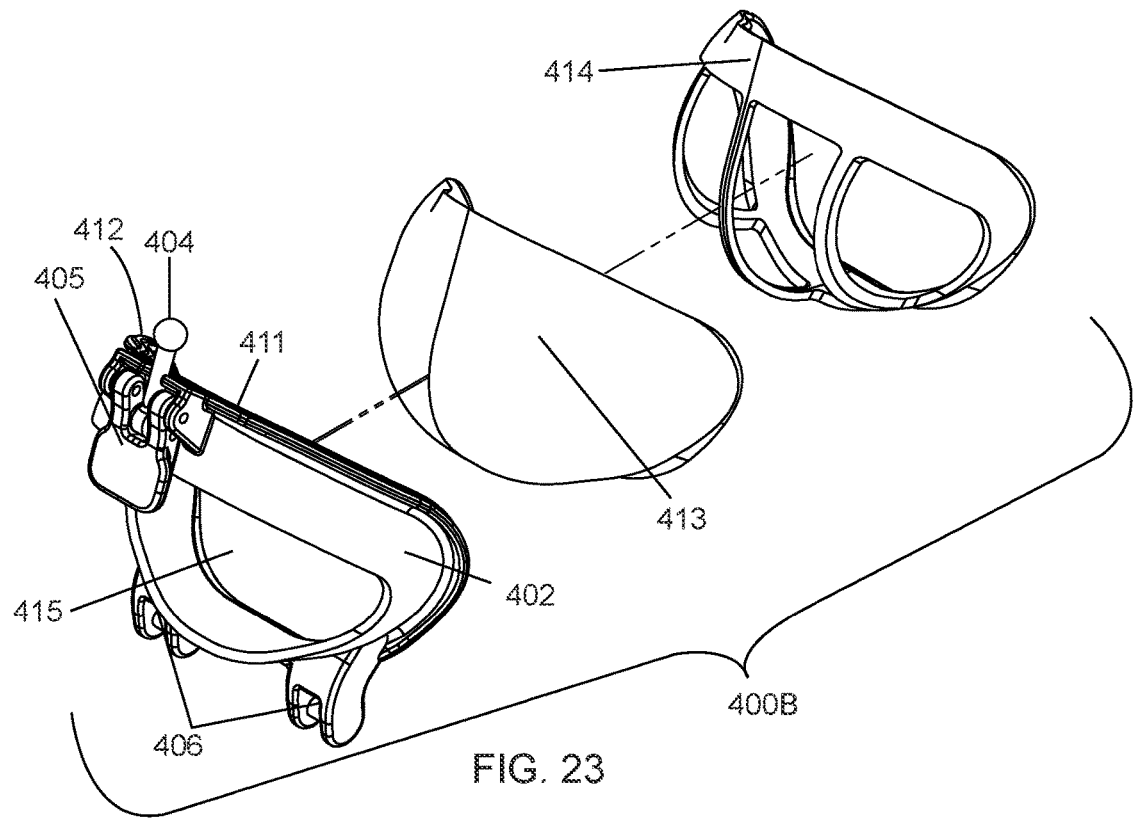

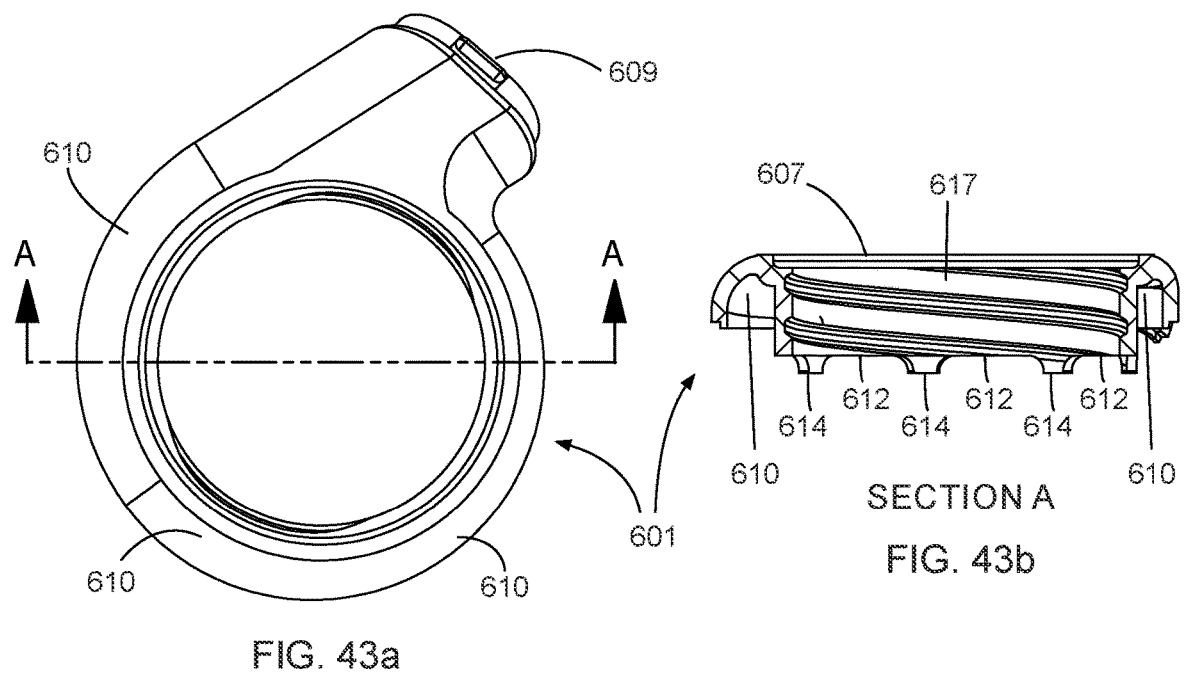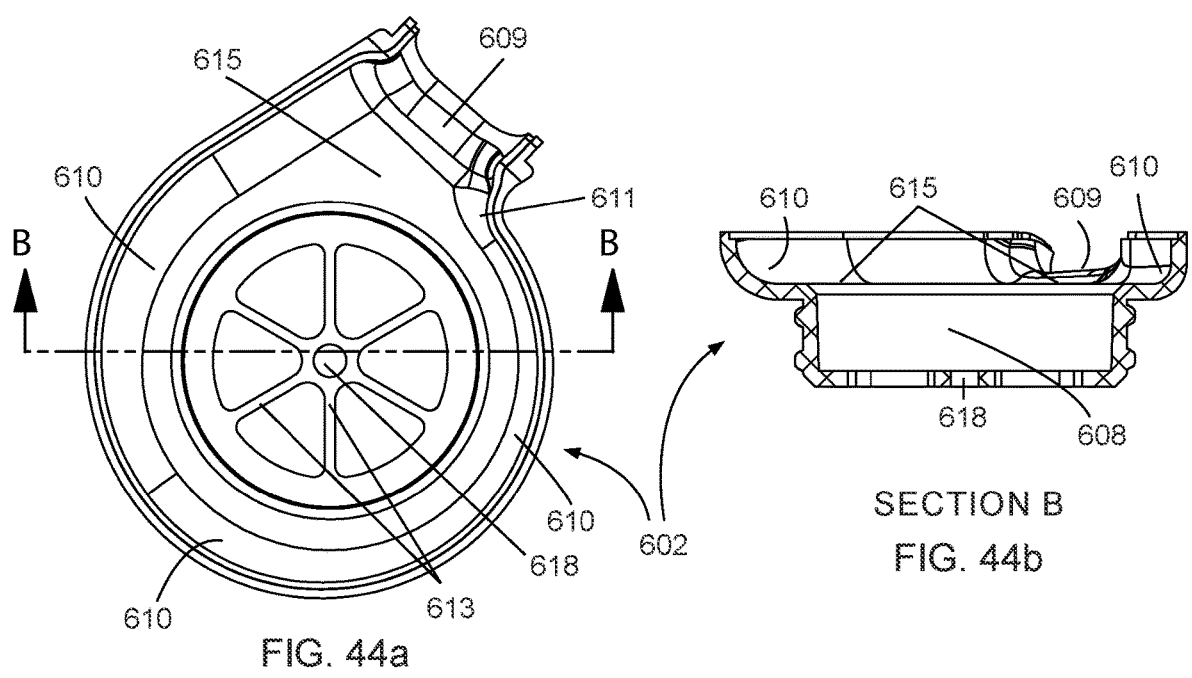

SECTION C

SECTION D

SECTION E

SECTION F

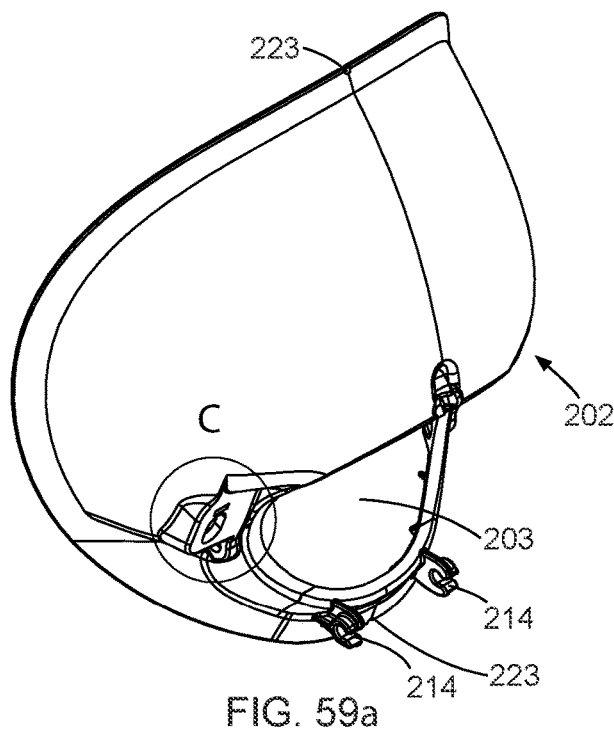
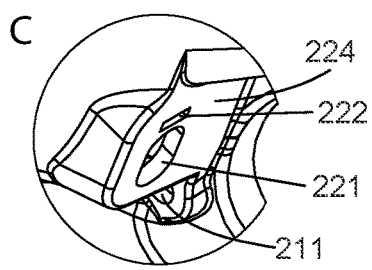
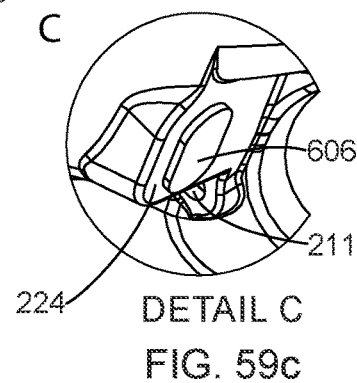
DETAIL C
FIG. 59b
FIG. 59a
DETAIL C
FIG. 59c
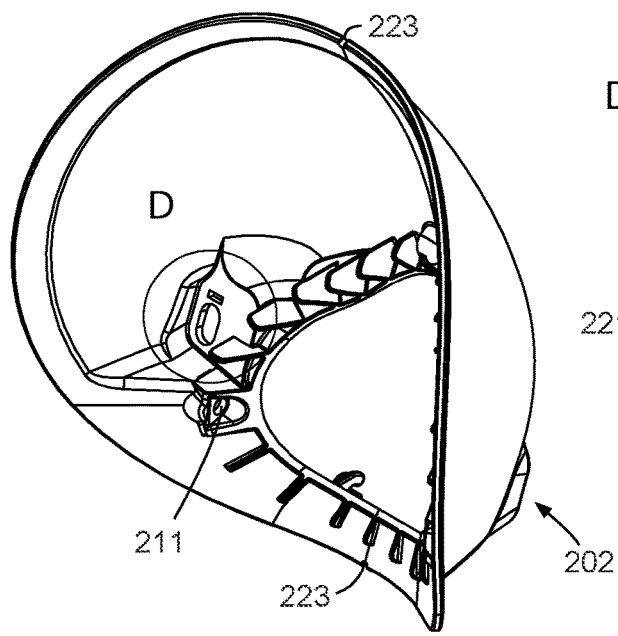
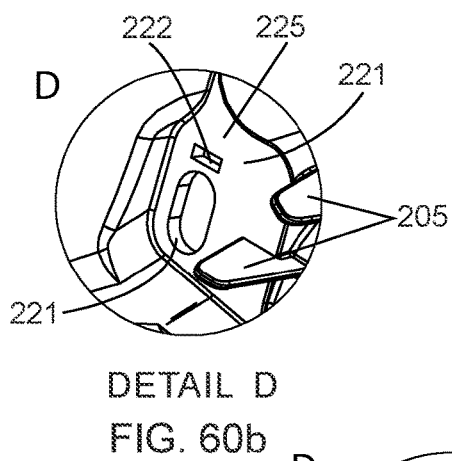
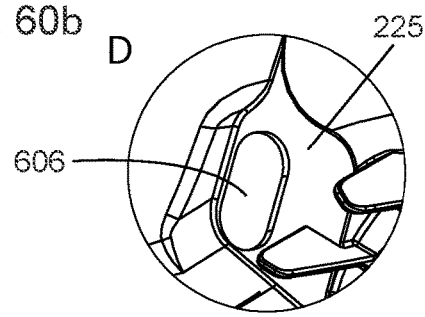
DETAIL D
FIG. 60b
FIG. 60a
DETAIL D
FIG. 60c

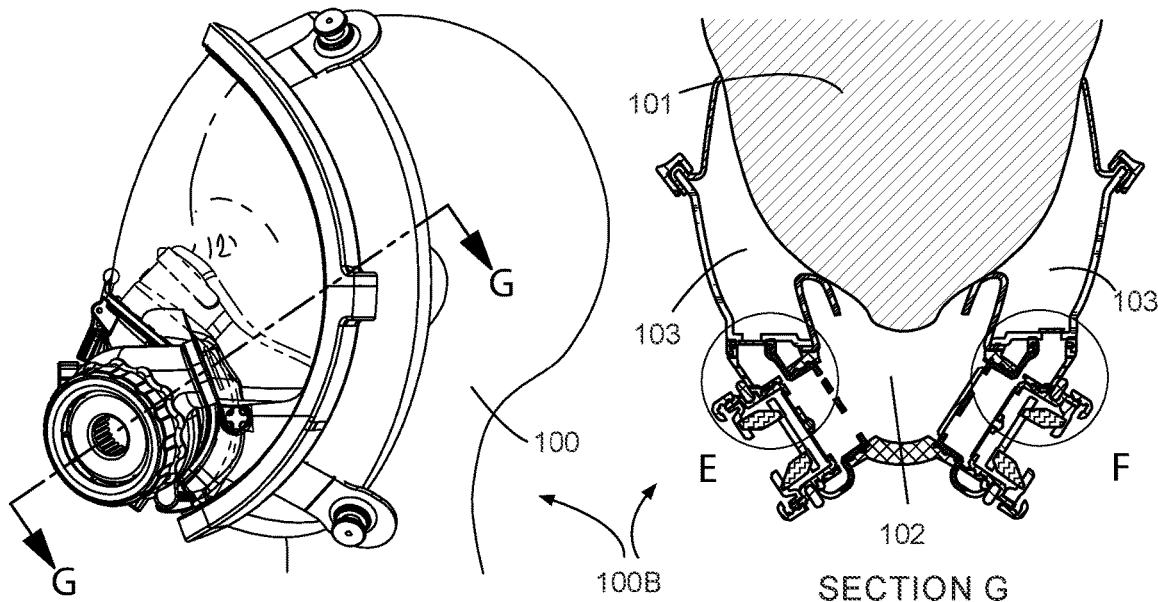
FIG. 61b
FIG. 61c
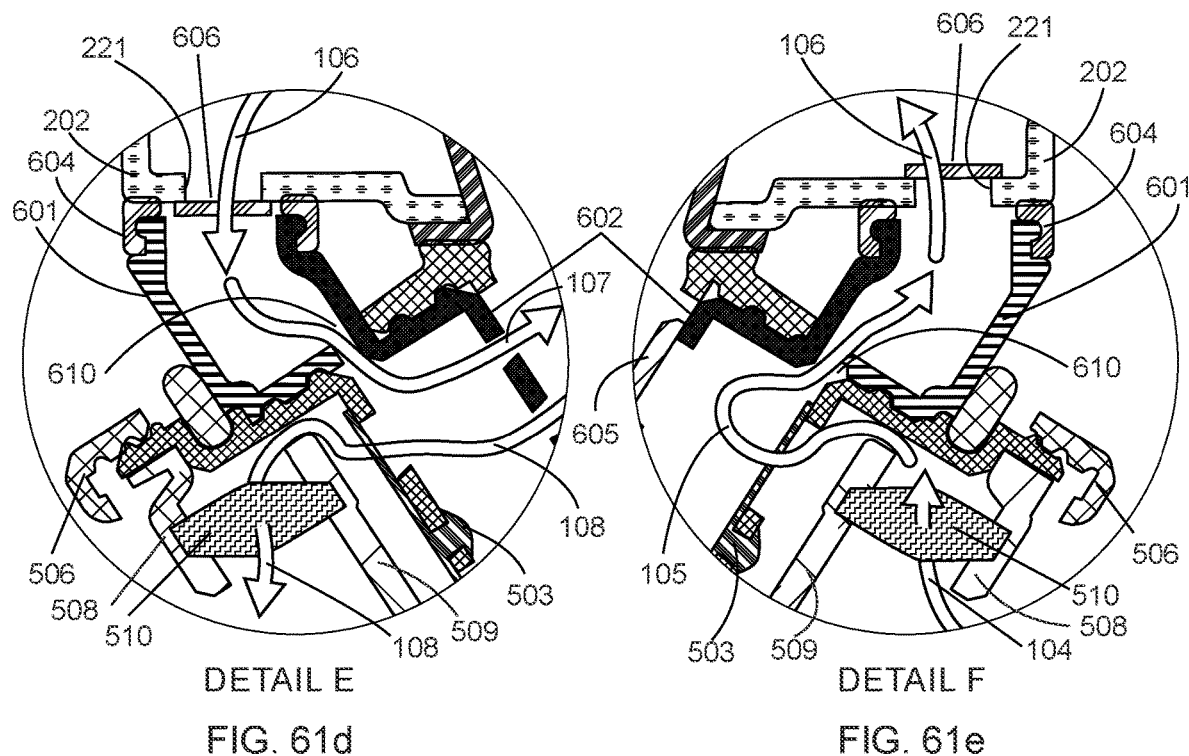
DETAIL E
FIG. 61d
DETAIL F
FIG. 61e

SERVICEABLE RESPIRATOR SYSTEM WITH CONFIGURABLE COMPONENTS

CROSS-REFERENCE TO RELATED APPLICATIONS

This application claims the benefit of U.S. Provisional Patent Application No. 63/057,143, filed Jul. 27, 2020, U.S. Provisional Patent Application No. 63/057,482, filed Jul. 28, 2020, and U.S. Provisional Patent Application No. 63/215,562, filed Jun. 28, 2021, which are incorporated by reference herein in their entireties.

TECHNICAL FIELD

The present disclosure generally relates to the field of personal protective equipment. Specifically, it relates to air purifying respirators.

BACKGROUND

Air purifying respirators (APR)s are a commonly known and utilized form of respiratory personal protective equipment (PPE). Respirators typically purify air via negative pressure (in which the user's inhalation draws air through a filter into the respirator) via 1) filtering facepieces or 2) detachable filter canisters/cartridges (herein cartridges). This is achieved by introducing fresh, filtered air through intake ports and advancing $CO_2$-rich, exhaled air out through exhaust valves into the environment. To facilitate this, half-face and whole-face respirators typically come with one-way valves to move air progressively through the respirator while preventing backwash. Further, some respirators come with components that allow the user to configure the respirator as a power-air purifying respirator (PAPR).

In applications where sterility is paramount, surgical-rated respirators are recommended, if not mandatory. Current surgical-rated masks address sterility for the wearer by forming a tight seal over the mouth and nose regions, in addition to filtering the wearer's inhaled and exhaled air. In many respirators, this function often results in a buildup of warm, humid air within the enclosure of the mask body, along with discomfort and fatigue of the wearer. While an exhaust port greatly aids in removing exhaust air from the mask, any respirator that utilizes an unfiltered exhaust valve that opens to the ambient air provides a potential ingress point for airborne pathogens to enter. Thus, the use of existing respirators in possession of an exhaust valve within sterile areas, such as surgical suites or in contaminated areas, brings an increased risk of exposure to both the wearer and the surrounding populace.

For respirators used within sterile areas or pathogen-contaminated areas, current designs do not account for rapid cleaning and sterilization within devices such as an autoclave, or even a dishwasher with sterilization capabilities. The use of an autoclave and similar sterilization devices ensure the respirator and its component parts are sterile each time the wearer dons the respirator system, which helps reduce the potential of contamination. For professions outside of the medicine that use respirators, the ability to thoroughly clean a respirator not only ensures the removal of grit and detritus, but also helps remove the odor that accumulates (e.g., body odor and breath odor) from long hours of work in potentially extreme conditions. To facilitate this, items designed for sterilization must possess the ability to be disassembled to the sub-component level, if not completely. This capability is not typically found in existing respirator designs.

BRIEF SUMMARY

In view of the above, there is an unmet need in the art for a serviceable respirator system with configurable parts.

The present disclosure affords such a respirator, which in brief summary comprises: (a) a frame assembly with mounting points for adjustable securing headgear and a sealing element to interface with the wearer's face; (b) a facepiece assembly with at least one orifice to allow air to pass between the interior gas space and the external environment, at least one filtering element, and at least one locking mechanism and attachment point; and (c) an adjustable securing headgear. In some embodiments, the facepiece assembly may comprise at least one filter port, a cartridge assembly, and a check valve to filter inhaled and exhaled air while preventing backwash. Further, the facepiece assembly may be configured with at least one port to accept accessories such as a hydration port, a sealed microphone and speaker assembly, or a flashlight. In yet a further embodiment, the facepiece assembly may utilize a reinforcing assembly to secure a filtering element across the opening of the facepiece with a secured seal to act as a negative-pressure respirator. Some embodiments of the facepiece assembly may include a port to secure an intubation hose in place for a patient on an external ventilator to ensure a secured seal between the patient and the external environment. The advantage of multiple facepiece assembly embodiments is that in addition to changing filter cartridges, the entire facepiece assembly may be swapped out either for a fresh copy of the unit in use (complete with new or cleaned filter cartridges) or for a different iteration based on changing situational requirements.

Continuing along this line, in some embodiments, the frame assembly may only include the sealing member and mounting points needed for the device to serve as a half-face respirator and seal the mouth and nose regions of the wearer from the external environment. In another embodiment, the frame assembly may comprise a face shield, faceplate/lens, or goggle assembly and sealing member, to fully isolate the wearer's full face from the external environment. This provides the dual benefit of configuring the systems of the present disclosure to serve as a full-face respirator while ensuring a greater commonality of parts between the two form configurations. In other embodiments, the full-face respirator configuration may comprise an adapter to redirect airflow from the cartridges into and through the interior lens space of the system before entering an interior mask space. The adapter of these embodiments ensures the sealing mask bodies may be used in both half-face and full-face configurations while also providing anti-fog, humidity control, and controlled airflow from the cartridge through the sealed lens areas into the interior gas space of the respirator.

The respirators of the present disclosure differ from known respirator systems by being able to either be partially or completely disassembled for servicing, reconfiguration, and (when applicable) cleaning and sterilization. In embodiments having the facepiece with filter cartridges, the filter cartridges themselves may be disassembled for cleaning or replacement of their filtering elements. Further, by placing the check valve on the filter cartridge rather than the facepiece or main assembly of the respirator, it becomes possible to configure the filter cartridge as a removable intake port or a removable exhaust port. This feature greatly simplifies the construction of the respirator and makes cleaning and sterilization significantly simpler. With the use of corrugated or folded filter mediums, having a self-contained cartridge with the check valve that inserts into the facepiece assembly provides the added benefits of reducing the size of the filter cartridge (resulting in a less obstructed field of view for the wearer compared to existing solutions, and by extension contributing to reduced mechanical dead space inside an oronasal mask. Additionally, to provide alternative means of air filtration in case of shortages or emergencies, a further embodiment may include fittings to permit the configurable and removable port elements to use existing filter cartridges available on the market in addition to those of the present disclosure.

Through the use of a sealing member on the oronasal mask; the leading edges of the frame and lens bodies at the oronasal openings; and the previously mentioned configurable facepieces with seals, filter mediums, and their attachment and locking mechanisms, the respirators of the present disclosure create a seal between the wearer's respiratory system and the external environment that will filter both inhaled (intake) and exhaled (exhaust) air. This greatly improves protection for both wearer and those around the wearer by preventing particles and other contaminants from passing between the wearer and the external environment. This is particularly beneficial for use in surgical procedures, clean rooms, and confined environments containing multiple individuals. In the case of the disclosed ventilator-adaptive facepiece, exhalation of contaminated air from the wearer's nostrils is prevented from entering the external environment by the facepiece and a sealing gasket while providing mechanical ventilation via devices such as ambu bags and intubation tubes.

One distinct advantage the present disclosure affords is a reduced interior gas space compared to existing designs. A true respirator system accounts not only the respirator device but the wearer's respiratory system as well. The human body's respiratory cycle generally consists of the inhalation of air that passes through the airways into the lungs where gas exchange occurs, after which $CO_2$ and other gasses are exhaled. This tidal volume of air may change based on level of physical exertion and overall bodily condition. Out of the total volume of air comprising the wearer's tidal volume, air can only undergo gas exchange within the alveoli of the lungs. The remainder of the respiratory system comprises the anatomical and physiological dead space, in which gas exchange cannot occur. This extends to the respirator itself, where the interior gas space of the respirator is considered mechanical dead space. Should the combined wearer-respirator dead space exceed the combined wearer-respirator air volume, either from mechanical limitation of the wearer's total lung volume resulting from injury or condition, or artificially by excessive mechanical dead space, the wearer risks respiratory discomfort at least, and at worst, asphyxiation. The placement of the filtering members within the negative-pressure filter and the check valves of the filter cartridge embodiment help limit the internal gas space of the respirator. As a result, the mechanical dead space element of the combined wearer-respirator dead space is decreased, resulting in a larger margin of safety for extended use and immuno-respiratory compromised wearers.

Further departing from known respirator systems, the filter cartridges of a cartridge facepiece embodiment may be configured to accept an adapter for existing filtering elements and for external, powered filtering elements. This significant feature allows the respirator to serve (when paired with the appropriate adapter) as: (a) a negative-pressure air-purifying respirator on its own; (b) a powered air-purifying respirator when hooked up to a powered air filtration device; (c) a filtering mask body for supplied air and self-contained breathing apparatus (SCBA) arrangements; (d) a filtering mask body for non-invasive ventilators such as ambu bags, continuous positive airway pressure (CPAP) and bilevel positive airway pressure (BPAP) machines; (e) a filtering mask body for invasive ventilators; and further still, (f) as a filtering mask body for medicine administration such as surgical anesthesia, nebulizer therapy, and asthma inhalers.

In a first aspect, a respirator for supplying clean air for a wearer to inhale is provided. The respirator comprises a face assembly including an oronasal mask configured to seal against and cover a nose region and a mouth region of the wearer. The face assembly may comprise a half-face assembly or a full-face assembly. The respirator may be configured such that the half-face assembly and the full-face assembly are interchangeable on the respirator. The facepiece assembly may be configured to releasably secure with one or more filter cartridges for filtering air.

The respirator comprises a securing headgear releasably securable with the face assembly, the securing headgear assembly configured to secure the respirator on a head of the wearer. The securing headgear may be adjustable, such as in length. The face assembly may comprise harness attachment elements, and the securing headgear may comprise one or more removable buckles configure to securely lock with the harness attachment elements.

The respirator comprises a facepiece assembly for supplying the wearer with air for inhaling and releasing air exhaled by the wear, the facepiece assembly releasably securable with the face assembly. The facepiece assembly may be releasably secured with the face assembly via an over center latch and a keeper bar. The facepiece assembly may be interchangeable on the face assembly between a cartridge facepiece assembly, a negative-pressure filter facepiece assembly, a ventilator-adaptive facepiece assembly, and an adapted cartridge facepiece assembly. The negative-pressure filter facepiece assembly may comprise a non-cartridge facepiece body, a breathing port, and a filter element secured by the non-cartridge facepiece body disposed between the breathing port and the wearer.

A lens may releasably securable with the face assembly, the lens configured to cover at least the eyes of the wearer when engaged with the face assembly. One or more of the face assembly, the facepiece assembly, or the securing headgear may be configured to be released from the respirator, sterilized, and releasably resecured with the respirator.

In a second aspect, a respirator for filtering air for a wearer is provided. The respirator comprises a full-face assembly configured to create a seal against a mouth region, a nose region, and an eye region and cover a mouth, a nose, and eyes of the wearer. The full-face assembly includes an interior gas space defined by the seal of the full-face assembly. The full-face assembly includes a lens releasably securable with the full-face assembly, the lens configured to cover at least the eyes of the wearer when engaged with the full-face assembly. The full-face assembly includes an oronasal mask configured to cover nose and mouth regions of the wearer, the oronasal mask releasably securable with the full-face assembly.

The respirator comprises an adapted cartridge facepiece assembly releasably securable with the full-face assembly. The adapted cartridge facepiece assembly includes a cartridge facepiece body and at least one adapter configured to direct airflow into the interior gas space through an intake filter cartridge and out of the interior gas space through an exhaust filter cartridge. The intake filter cartridge and the exhaust filter cartridge may be releasably secured with the adapted cartridge facepiece assembly, and the at least one adapter is disposed and in gaseous communication between the cartridge facepiece body, the intake filter cartridge, and the exhaust filter cartridge. The adapted cartridge facepiece assembly and the full-face assembly may be releasably secured via a keeper bar and an over center latch. The respirator may comprise one or more anti-fog check valves configured to direct a flow of air into, through, and out of the interior gas space. One or more of the full-face assembly, the adapted cartridge facepiece assembly, or the adapter may be configured to be released from the respirator, sterilized, and releasably resecured with the respirator.

In a third aspect, a respirator for supplying clean air for a wearer in need of assisted breathing is provided. The respirator comprises a face assembly defining an interior gas space, the face assembly including a mask configured to seal against and cover at least a nose region and a mouth region of the wearer. The respirator comprises a facepiece assembly for supplying the wearer with air for inhaling and releasing air exhaled by the wear. The facepiece assembly is releasably securable with the face assembly mask and interchangeable on the respirator between two or more of a cartridge facepiece assembly, a negative-pressure filter facepiece assembly, a ventilator-adaptive facepiece assembly, and an adapted cartridge facepiece assembly. The facepiece assembly may comprise the ventilator-adaptive facepiece assembly, the ventilator-adaptive facepiece assembly including a port configured to be in gaseous communication with the interior gas space. The port may be configured to seal with at least one of an intubation tube, an air hose, or an ambu bag. One or more of the face assembly and the facepiece assembly are configured to be released from the respirator, sterilized, and releasably resecured with the respirator.

Thus, the present disclosure provides a serviceable respirator system that may be configured to the wearer's needs, is capable of partial and complete disassembly for cleaning and servicing, and filters and seals both the inhaled and exhaled air of the wearer. This affords a respirator system that may be utilized by a larger variety of different fields and applications than existing designs.

BRIEF DESCRIPTION OF THE DRAWINGS

The objects, features, and advantages of the present disclosure will become better understood regarding the following description and accompanying drawings, wherein:

FIG. 21 is a front view of a negative-pressure filter facepiece assembly 400B, in accordance with an embodiment;

FIG. 22 is a rear view of the negative-pressure filter facepiece assembly 400B shown in FIG. 21;

FIG. 23 is an exploded view of the negative-pressure filter facepiece assembly 400B, shown in FIG. 21;

FIG. 27a is a midline cross-sectional view of a half-face assembly 200A and cartridge facepiece assembly 400A, where the serviceable respirator system is in a closed and secured position in accordance with an embodiment;

FIG. 27b is a midline cross-sectional view of a half-face assembly 200A and cartridge facepiece assembly 400A, where the cartridge facepiece assembly 400A is in a closed position with over center latch 405 disengaged in accordance with an embodiment;

FIG. 27c is a midline cross-sectional view of a half-face assembly 200A and cartridge facepiece assembly 400A, where the cartridge facepiece assembly 400A is in a closed position with both the over center latch 405 and keeper bar 404 disengaged from the system in accordance with an embodiment;

FIG. 27d is a midline cross-sectional view of a half-face assembly 200A and cartridge facepiece assembly 400A, where the cartridge facepiece assembly 400A is in an open, captive position in accordance with an embodiment;

FIG. 27e is a midline cross-sectional view of a half-face assembly 200A and cartridge facepiece assembly 400A, where the cartridge facepiece assembly 400A is disengaged from the half-face assembly 200A in accordance with an embodiment;

FIG. 43a is a top view of the cartridge side housing 601 of the adapter assembly 600 with Section Line A, in accordance with an embodiment;

FIG. 43b shows a cross-sectional view of the cartridge housing 601 along Section Line A; in accordance with an embodiment;

FIG. 44a is a top view of the respirator side housing 602 of the adapter assembly 600 with Section Line B, in accordance with an embodiment;

FIG. 44b shows a cross-sectional view of the respirator side housing 602 along Section Line B, in accordance with an embodiment;

FIG. 59a shows the full-face lens 202 in a front perspective view with Detail C, in accordance with an embodiment;

FIGS. 59b and 59c are enlarged views of Detail C, illustrating the anti-fog check valve elements. FIG. 59b shows the anti-fog aperture 221, while FIG. 59c shows the installation of the anti-fog check valve 606 in an exhaust configuration in accordance with an embodiment;

FIG. 60a shows the full-face lens 202 in a rear perspective view with Detail D; in accordance with an embodiment;

FIGS. 60b and 60c are enlarged views of Detail D, illustrating the anti-fog check valve elements. Specifically, FIG. 60b shows the anti-fog aperture 221 while FIG. 60c shows the installation of the anti-fog check valve 606 in an intake configuration in accordance with an embodiment;

FIGS. 61a through 61e illustrate the airflow through the full-face respirator 100B configuration of the serviceable respirator system in accordance with an embodiment;

FIG. 61a is a perspective view of the full-face respirator 100B as worn (with securing headgear 300B omitted for clarity) which illustrates the flow of air through the system in accordance with an embodiment;

FIG. 61b is a side view of the full-face respirator 100B as worn (with securing headgear 300B omitted for clarity) with Section Line G, in accordance with an embodiment;

FIG. 61c is a cross-sectional view of the full-face respirator 100B shown in FIG. 61b along Section Line G, and is used to describe the location of interior gas spaces as well as establish the locations of Detail E and F, in accordance with an embodiment;

FIG. 61d is an enlarged Detail E, continuing the illustration of airflow through the full-face respirator 100B established in FIG. 61a, in accordance with an embodiment; and FIG. 61e is an enlarged Detail F, continuing the illustration of airflow through the full-face respirator 100B established in FIG. 61a, in accordance with an embodiment.

DETAILED DESCRIPTION

Glossary

Figure 1:
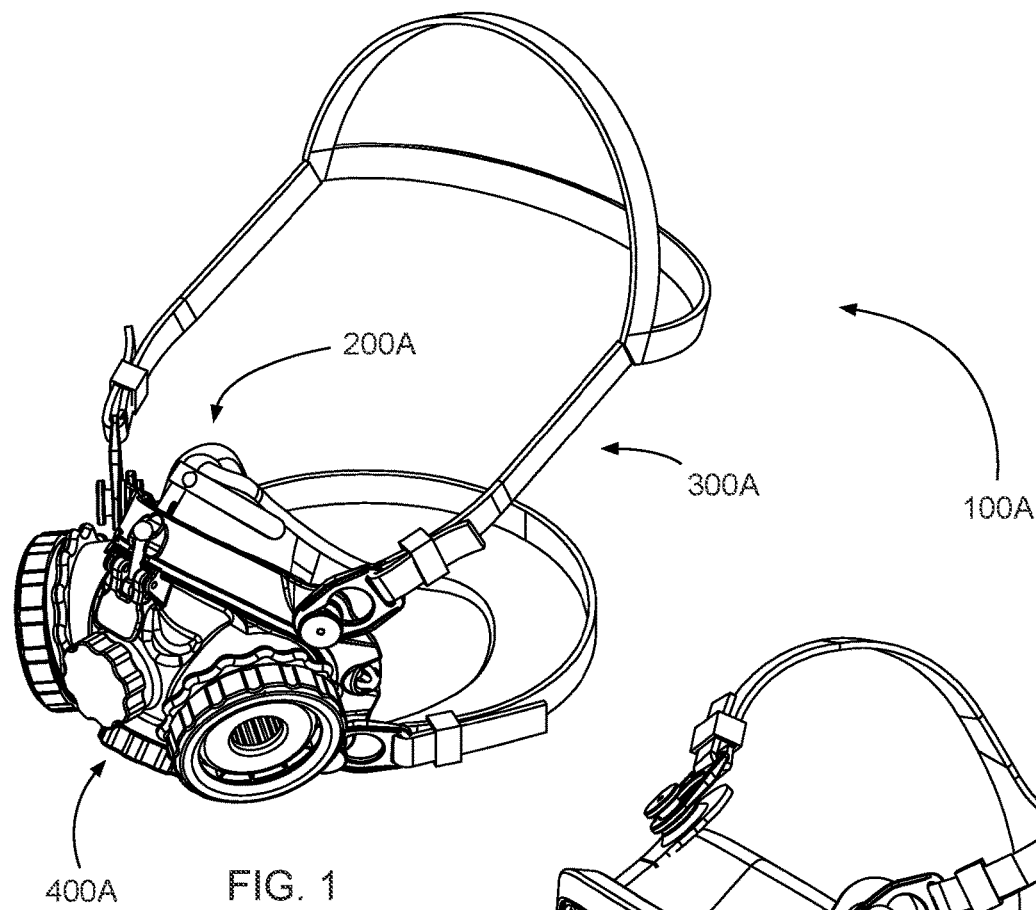
FIG. 1 is a front perspective view of a serviceable respirator system in half-face configuration 100A with half-face assembly 200A, cartridge facepiece assembly 400A, and half-face securing headgear 300A, in accordance with an embodiment.

While most terms are commonly understood within the art, in reference to the present disclosure, the following terms (both those commonly understood within the art and those specific to the present disclosure) are defined as set forth below:

"aerosol" means a gas that contains suspended particles in solid and/or liquid form;

"air-purifying respirator," or APR, refers to a piece of protective equipment worn to prevent hazardous airborne particulates from being inhaled by the wearer;

"anatomical dead space" means the volume of air in the conducting airways in which air does not undergo significant gaseous exchange;

"check valve" means any device used to automatically limit flow to a single direction;

"clean air" means a volume of air that has been filtered to remove contaminants;

"combined wearer-respirator dead space," or "CWRDS," refers to the combined volumes of the wearer's total dead space (anatomical plus physiological) and the respirator's interior gas space (TDS+IGS);

"combined wearer-respirator volume," or "CWRV," refers to the combined volumes of the wearer's total dead space, the wearer's total lung volume, and the respirator's interior gas space (TDS+TLC+IGS): i.e., the total amount of air available to the wearer's respiratory system which is separated from the external environment by the respirator and its component parts;

"contaminant" means particles and/or other substances that generally are not considered to be particles (e.g., organic vapors, et cetera) that may be suspended in the ambient air and exhaled air from the wearer.

"exhaled air" means a volume of warm, humid, $CO_2$-rich air which is exhaled by the wearer as part of the respiratory cycle;

"exhaust air" means a volume of air, i.e., the exhaled air from the wearer that is expelled from the interior gas space of a respirator system through the orifice of an exhaust port into the external environment;

"exhaust port" refers to an egress point, i.e., the orifice through which exhaust air may exit the interior gas space of the respirator;

"external environment" means the ambient air external to the interior gas space of the respirator;

"face seal" means a structure engaged with a respirator and fitting over portions of at least one of the wearer's face, head and jaw. The face seal may define a collective interior gas space comprising an interior lens space and interior mask space that is separated from an exterior gas space such as the ambient air of the external environment;

"filter cartridge" means an assembly holding a filtering element that can be installed and removed from the mask body of a respirator;

"filter element" means a structure through which air can pass and which is configured to remove contaminants from the directional airflow. A filter element may be used to filter intake air, exhaust air, or both;

"gaseous communication" means two or more features that are configured such that air or gas may flow, or otherwise can be freely exchanged, between them;

"inhaled air" means a volume of air that is inhaled by the wearer as part of the respiratory cycle;

"intake air" means a volume of air, i.e., the inflow of air brought into the interior gas space of a respirator system from the external environment through the orifice of a filtered intake port, resulting in the clean inhaled air that is inhaled by the wearer;

"intake port" refers to an ingress point, e.g., the orifice through which intake air may enter the interior gas space of the respirator;

"interior gas space," or "IGS," means the volume of mechanical dead space in a respirator. The wearer inhales air from the IGS and exhales air into the IGS;

"interior lens space," or "ILS," means the volume of interior gas space between the oronasal mask, the face of the wearer, and the face lens of a full-face respirator system;

"interior mask space," or "IMS," means the specific volume of interior gas space within the oronasal mask and the rigid elements of the respirator body;

"mechanical dead space" means the volume of air within an apparatus or device external to the wearer's respiratory system in which air does not undergo significant gaseous exchange as part of the respiratory cycle;

"region" in conjunction with an anatomical feature (e.g., nose region, mouth region, eye region) refers to that anatomical feature and an area proximate to that anatomical feature;

"oronasal" means the region of the human head proximate to the mouth and nose, including the mouth and nose;

"oronasal mask" means a structure engaged with a respirator and fitting over the nose and mouth regions of the wearer, which helps to define an interior gas space that is separated from an exterior gas space, such as the ambient air of the external environment;

"particle" means any liquid and/or solid substance that is capable of being suspended in air, for example, pathogens, bacteria, viruses, mucous, saliva, blood, etc.

"physiological dead space" means the volume of air of the lungs in which air does not undergo significant gaseous exchange;

"powered air-purifying respirator," or "PAPR," refers to a piece of protective equipment worn to prevent potentially hazardous airborne particulates from being inhaled by the wearer, and which uses a powered system to pull ambient air through a purifying device and into the user's breathing zone;

"respirator" means a mask or device worn at minimum over the mouth and nose to protect the respiratory system by filtering out potentially dangerous substances (such as aerosols, contaminants, and particles) from inhaled air;

"tidal volume" means the volume of air inhaled or exhaled in a normal breath as part of the respiratory cycle;

"total dead space," or "TDS," means the total volume of air within the respiratory system that is inhaled and does not take part in the gas exchange, such as air that remains in the conducting airways or reaches alveoli that are not perfused or poorly perfused;

"total lung volume," or "TLV," refers to a measurement of the total amount of air that the lungs can hold, i.e., the sum of the residual volume, expiratory reserve volume, tidal volume, and inspiratory reserve volumes (RV+ERV+TV+IRV);

"ventilator" means a device that enables the delivery or movement of air and oxygen into the lungs of an individual, particularly patients whose breathing has ceased, is failing, or is inadequate; and "wearer in need of assisted breathing" means a subject, which may be an animal, a human, a male, a female, a child, or an adult, for whom a medical determination has been made that the subject medically requires an assisted breathing apparatus, such as mechanical ventilation, that moves gas into and out of the lungs of the subject by an external source connected to the patient.

The present disclosure has utility with many types of respirators: half-face respirators that cover the wearer's nose and mouth; full-face respirators that cover the wearer's nose, mouth, and eyes; full body suits and hoods, powered and supplied air masks, self-contained breathing apparatus, and essentially any other filtering face mask that may be fitted with an intake and exhaust port. The respirators, and their components, are particularly suitable as, or for use with, with half-face and full-face respirators, and find use with subjects who may not need assistance breathing and subjects in need of breathing assistance.

Figure 2:
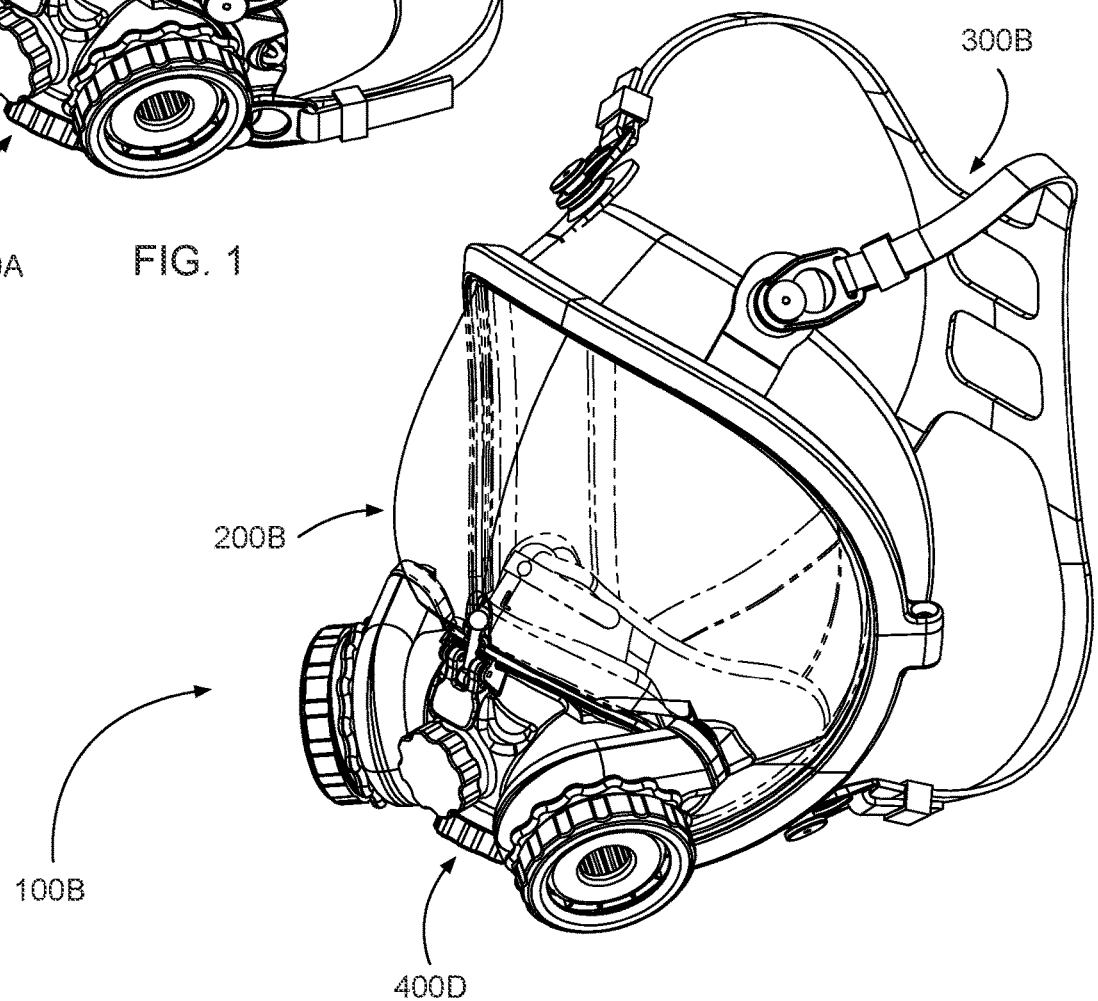
FIG. 2 is a front perspective view of a serviceable respirator system in full-face configuration 100B with full-face assembly 200B, adapted cartridge facepiece assembly 400D, and securing headgear 300B, in accordance with an embodiment.
Figure 3:
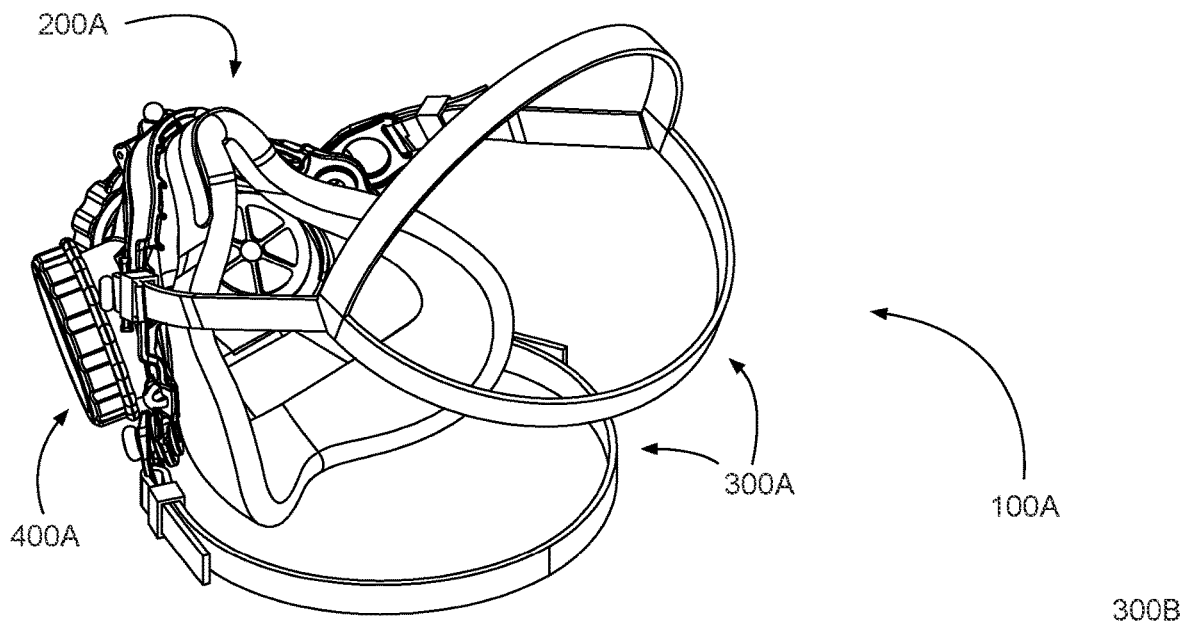
FIG. 3 is a rear perspective view of a serviceable respirator system in half-face configuration 100A with half-face assembly 200A, cartridge facepiece assembly 400A, and half-face securing headgear 300A, in accordance with an embodiment.
Figure 4:
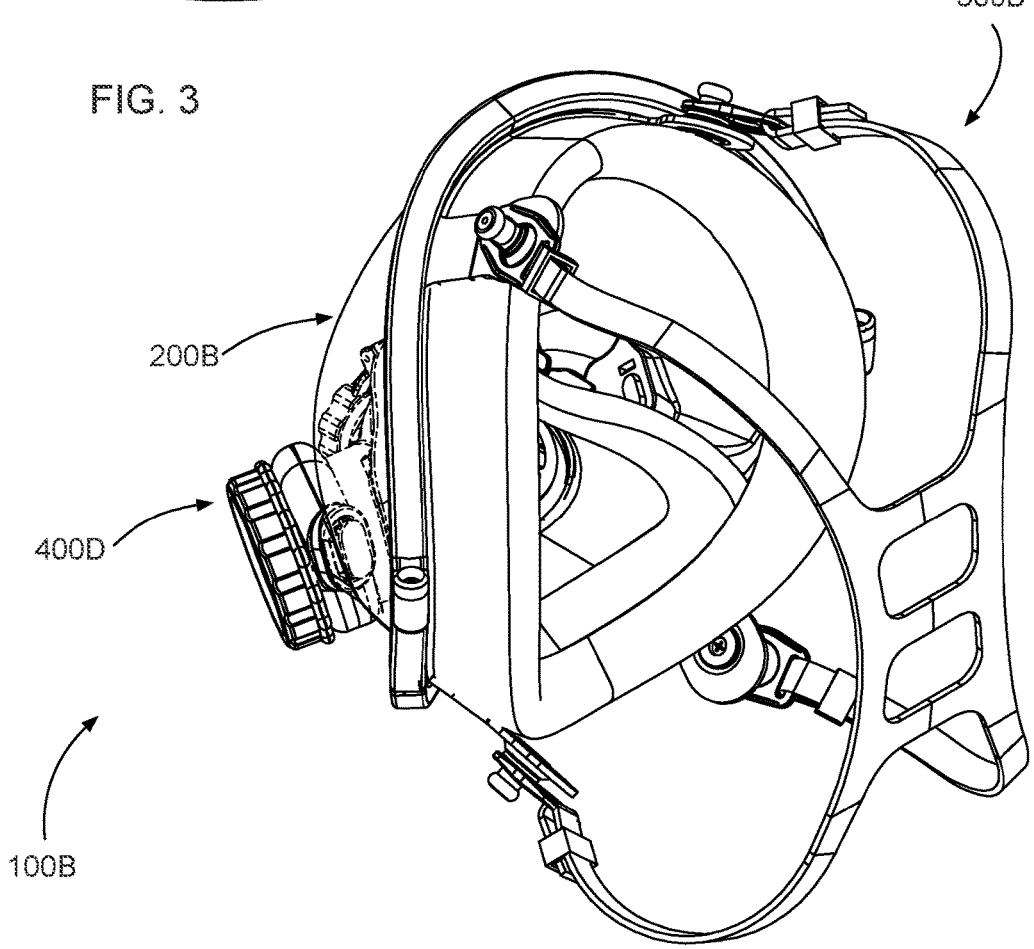
FIG. 4 is a rear perspective view of a serviceable respirator system in full-face configuration 100B with full-face assembly 200B, adapted cartridge facepiece assembly 400D, and securing headgear 300B, in accordance with an embodiment.
Figure 5:
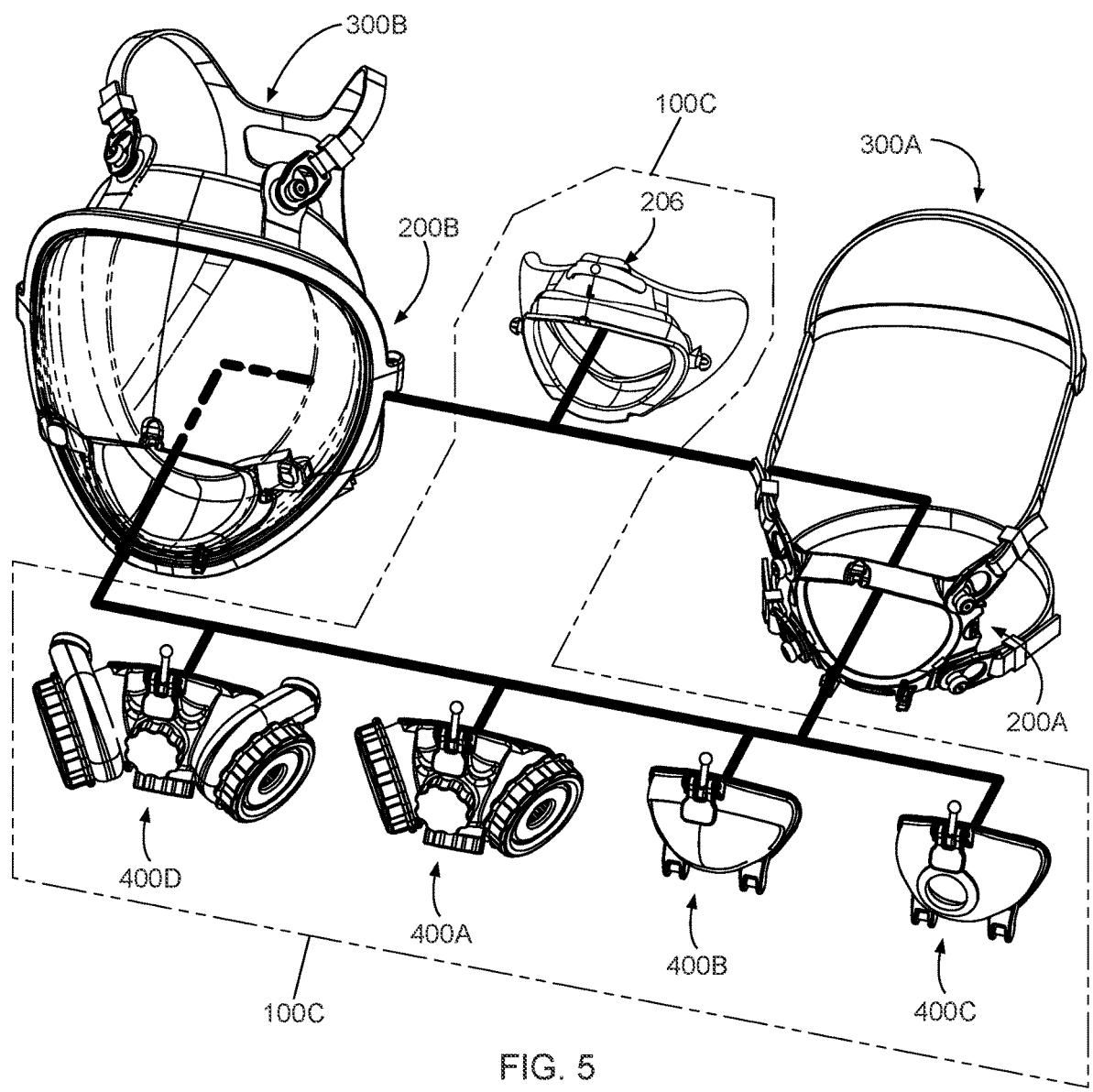
FIG. 5 illustrates a serviceable respirator with configurable parts, where the common parts of an oronasal mask 206 and facepiece assemblies 400A-400D are shown with their possible configurations with a half-face assembly 200A and full-face assembly 200B in accordance with an embodiment.
Figure 6:
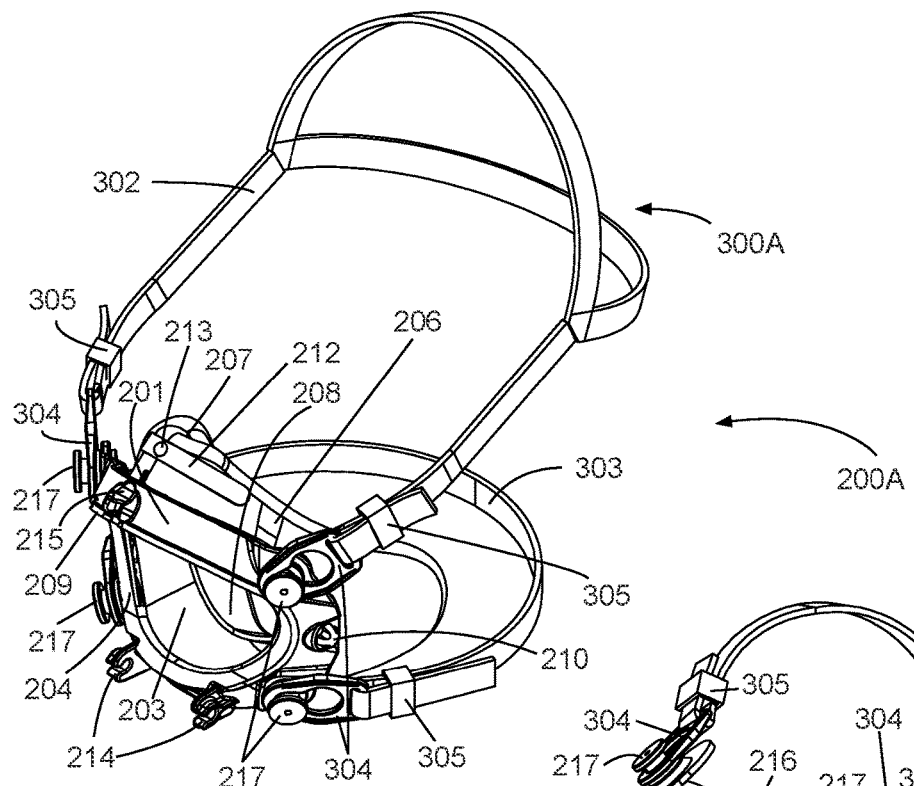
FIG. 6 is a perspective view of a serviceable respirator system illustrating the half-face assembly 200A and securing headgear 300A elements that interface with the wearer's head, in accordance with an embodiment.
Figure 7:
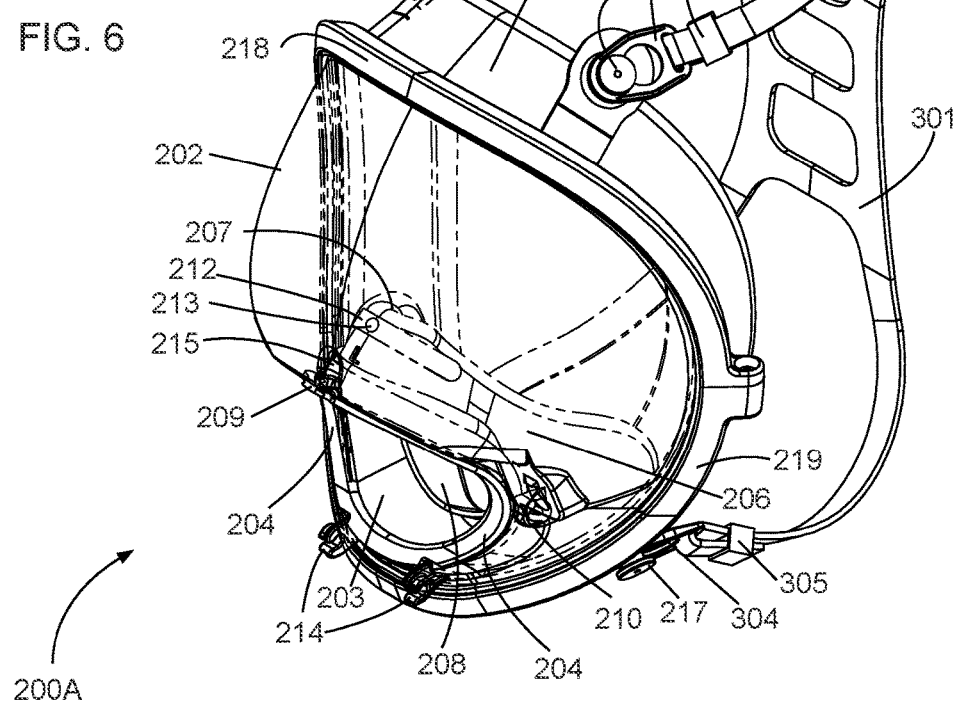
FIG. 7 is a perspective view of a serviceable respirator system illustrating the full-face assembly 200B and securing headgear 300B elements that interface with the wearer's head, in accordance with an embodiment.
Figure 8:
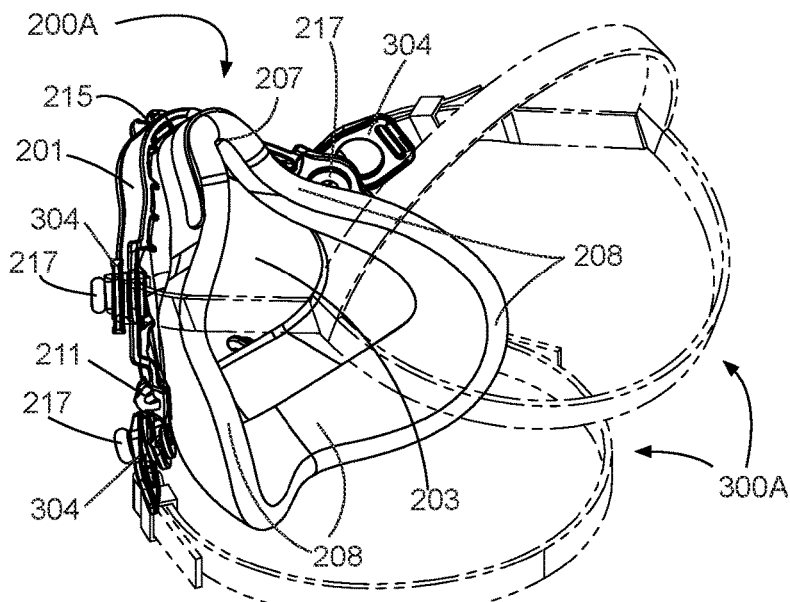
FIG. 8 is a rear perspective view of a serviceable respirator system illustrating the half-face assembly 200A and securing headgear 300A elements that interface with the wearer's head (with headgear 300A shown in broken lines for clarity), in accordance with an embodiment.
Figure 9:
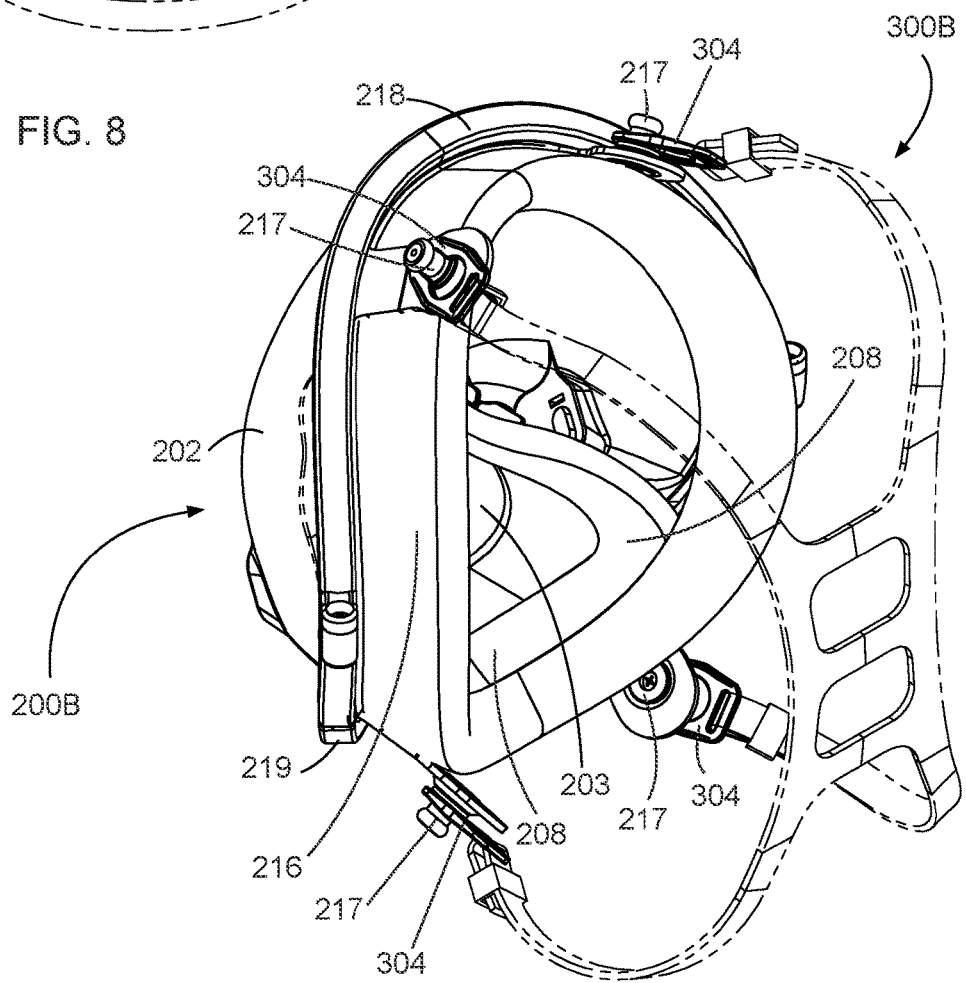
FIG. 9 is a rear perspective view of a serviceable respirator system illustrating the full-face assembly 200B and securing headgear 300B elements that interface with the wearer's head (with headgear 300B hidden shown in broken lines for clarity), in accordance with an embodiment.

FIGS. 1 through 5 illustrate the respirator system 100A/100B in its two main configurations and with its major assemblies. When assembled, the respirator system 100A/100B can supply clean air for a wearer to inhale. The respirator system may comprise a face assembly 200A/200B. In FIG. 1 and FIG. 3, a half-face respirator 100A is shown according to one embodiment, comprising a half-face assembly 200A, a headgear 300A, and a cartridge facepiece assembly 400A. FIG. 2 and FIG. 4 illustrate a full-face respirator 100B with full-face assembly 200B, headgear 300B, and a releasably securable adapted cartridge facepiece assembly 400D. FIG. 5, by comparison, shows the major assemblies of the respirator system. The half-face assembly 200A and the full-face assembly 200B may be interchangeable on the respirator system 100A/100B such that the face assemblies 200A/200B may be swapped out with another, such that the respirator system may transition from the half-face respirator 100A to the full-face respirator 100B and vice versa. Specifically, FIG. 5 shows an oronasal mask 206 and the facepiece assemblies 400A-400D make up common parts 100C of the system, which are interchangeable between half-face and full-face configurations. Common parts include, for example, a securing headgear 300A/300B. To adapt the common parts 100C for use in either a half-face respirator 100A or a full-face respirator 100B, the appropriate half-face assembly 200A and half-face securing headgear 300A or full-face assembly 200B and full-face securing headgear 300B are be selected. This use of common parts 100C with half- and full-face subassemblies helps standardize components between the different configurations, making it easier for the user to replace aging or broken component parts, and streamlining the manufacturing and logistical chain tracking the individual elements that make up the serviceable respirator described herein.

Figure 10:
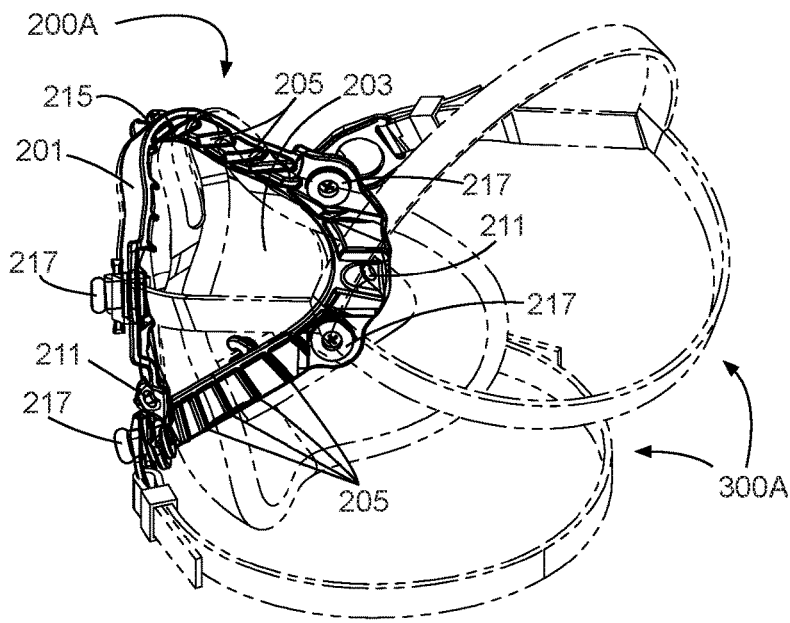
FIG. 10 is a rear perspective view illustrating the frame body 201 in the context of the half-face assembly 200A with headgear and oronasal mask shown in broken lines, in accordance with an embodiment.
Figure 11:
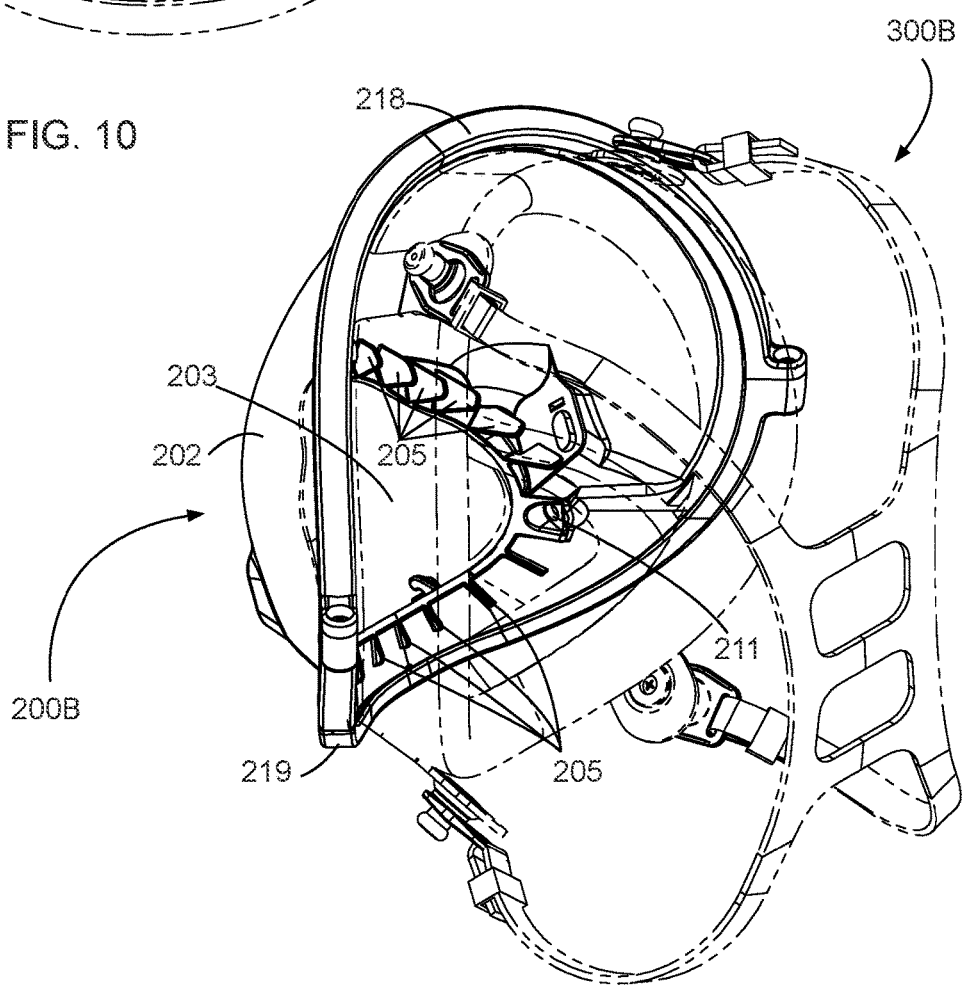
FIG. 11 is a rear perspective view illustrating the full-face lens 202 in the context of the full-face assembly 200B with headgear and sealing masks shown in broken lines, in accordance with an embodiment.

FIGS. 6 through 9 show the elements physically interfacing with the face of the wearer. FIGS. 10 through 11 detail the interior elements of a frame body 201 and a full-face lens 202 that interface with (e.g., releasable secure with) the oronasal mask 206. The oronasal mask 206, in some embodiments, fits over the nose and mouth of the wearer, with a sealing oronasal flange 208 and a nose contour notch 207 providing a comfortable and secure seal to the wearer's face. For a more comfortable and secure fit, a nose bridge clip 212, which is secured to the oronasal mask 206 via a nose bridge clip stem 213, may be bent to conform to the wearer's nose and prevent an over-pressure leak from the mask 206. A forward facepiece sealing flange 209 fits inside of an oronasal opening 203 of both the frame body 201 and full-face lens 202, and is secured to the frame body 201 or full-face lens 202 via an oronasal mounting stem 210 being inserted into an oronasal mounting stem port 211. To allow for different sized oronasal masks 206 (which may accommodate sizes comprising at least Small, Medium, and Large), the sealing flange 209 and the elements of the oronasal mask 206 that interact with either the frame body 201 or full-face lens 202 are standardized to the largest user size, allowing the sealing oronasal flanges 208 of differing size bodies to be interchanged. To reduce weight of the frame body 201 and full-face lens 202, mask supporting ribs 205 are placed on the inner faces of the respective frame body 201 and full-face lens 202, allowing the oronasal mask 206 to be securely held in location, while the oronasal mounting stem 210 and the compressive force of the facepiece assemblies 400A-400D provide a positive means of removable fastening for the oronasal mask 206.

To don the respirator in half-face configuration 100A, an upper harness strap 302 is placed atop and to the rear of the wearer's head while a lower harness strap 303 is placed around the nape of the neck. Securing the upper harness 302 and lower harness 303 to the half-face assembly 200A are harness buckles 304, which mount to two-part harness attachment elements 217, such as buttons or any other suitable fastener. To don the respirator in full-face configuration 100B, a full harness body 301 with buckles 304 mount to two-part harness attachment elements 217 attached to a full face seal 216. Further adjustment may be accomplished by an adjustable slider 305, should its functionality not be integrated into the buckles 304 as a standardized part. By sharing components between half- and full-face configurations 100A/100B with regard to the headgear, the number of standardized, interchangeable parts is increased, while ensuring the donning and doffing procedure remains the same.

Pertaining to the removable fastening means of the facepiece assembly referred to above for releasably securing the facepiece assemblies 400A-400D with the face assemblies 200A/200B, FIGS. 12a, 12b, 13a, and 13b illustrate the locking elements for the facepiece assemblies 400A-400D to a half-face assembly 200A or full-face assembly 200B. Once the facepiece assembly (shown here as 400A) is closed and secured via an over center latch 405 and a keeper bar 404 engaging with a keeper notch 215 of the half face frame 201, the oronasal mask 206 with its sealing oronasal flange 208 and facepiece flange 209 provide the secure seal to the system and help establish an interior gas space (specifically the interior mask space) of the respirator. For securing the respirator 100A/100B to the head and face of the wearer, the securing headgear 300A/300B is held in place by removable, swiveling buckles 304 on the securing headgear 300A/300B that lock onto two-part harness attachment elements 217 on the face assembly 200A/200B that are either fastened onto the frame body 201 or secured into their respective ports on the face seal 216. This arrangement permits quick donning and doffing of the respirator 100A/100B and disassembly of the headgear 300A/300B for cleaning and servicing. The securing headgear 300A/300B may be further adjusted, such as in length to adjust tightness with the wearer's head, to personal preference via the adjustable slider 305.

The frame and lens features shown in FIGS. 1 through 15 provide significant advantages. Both half-face assembly 200A and full-face assembly 200B include annular hinge knuckle points 214 and the keeper notch 215 arrangement to accept different facepiece assemblies 400A-400D. Further, they both include the oronasal mask 206 (one of the common parts 100C of the system), which is the component part specifically sized to fit various wearer size groups while still accommodating the same mounting features and dimensions in that region as previously described. FIGS. 6 through 9 show the oronasal mask 206 with the nose contour notch 207 and the nose bridge clip 212. The half-face assembly 200A and the full-face assembly 200B differ in that the full-face lens 202 and face seal 216 enclose and define an interior lens space to seal the face and eyes from the external environment.

Figure 12A:
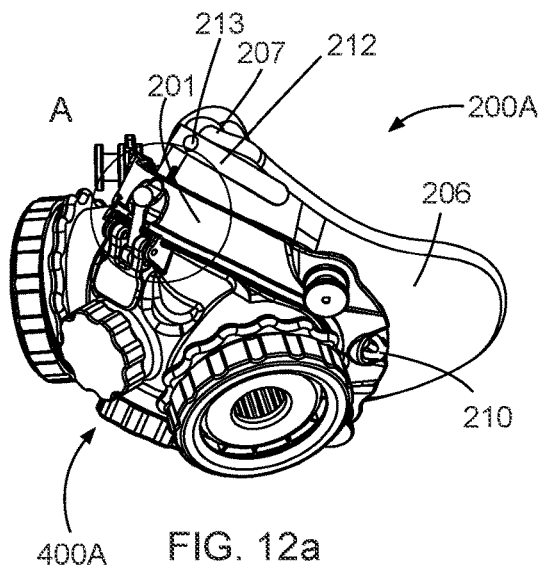
FIG. 12*a* is a perspective view with Detail A of the half-face assembly 200A and facepiece assembly, specifically a cartridge facepiece assembly 400A, in accordance with an embodiment.
Figure 12B:
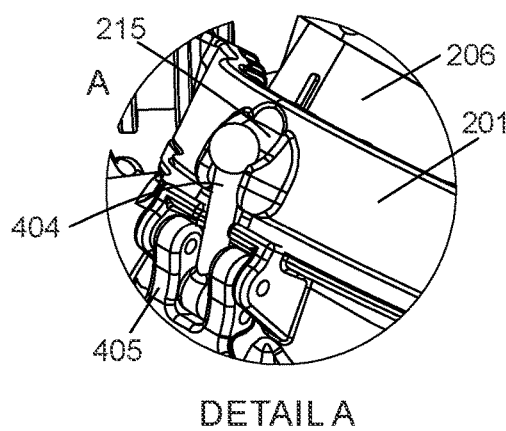
FIG. 12*b* is an enlarged view of Detail A of the half-face assembly 200A and cartridge facepiece assembly 400A, illustrating the locking mechanism and interface between the two assemblies in accordance with an embodiment.
Figure 13A:
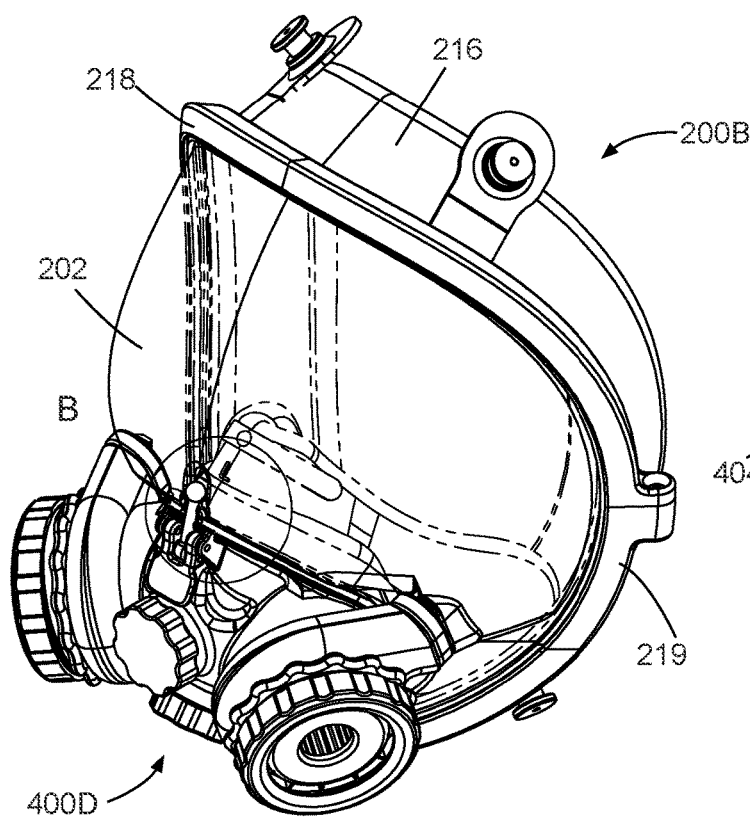
FIG. 13*a* is a perspective view with Detail B of the full-face assembly 200B and facepiece assembly, specifically an adapted cartridge facepiece assembly 400D, in accordance with an embodiment.
Figure 13B:
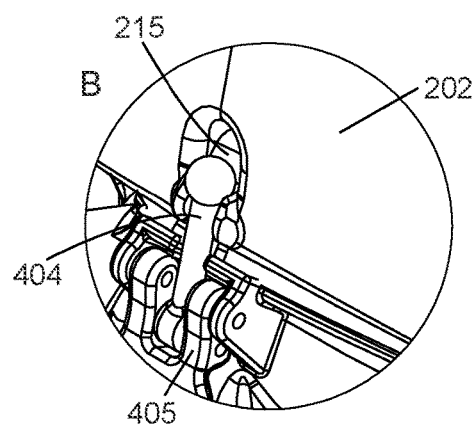
FIG. 13*b* is an enlarged view of Detail B of the full-face assembly 200B and adapted cartridge facepiece assembly 400D, illustrating the locking mechanism and interface between the two assemblies in accordance with an embodiment.

FIG. 12b shows an enlarged view of the Detail A identified in FIG. 12a, while FIG. 13b shows a similar enlarged view of Detail B from FIG. 13a. From these views, one can see how the over center latch 405 and keeper bar 404 are attached to facepiece assemblies 400A/400D, and how the keeper bar 404 contacts the frame body 201 and full-face lens 202.

To ensure a positive lock, a concave keeper notch 215 is cut into the frame body 201 and full-face lens 202. The keeper notch 215 may be slightly larger on the full-face assembly 200B, so the keeper bar 404 may swing unimpeded out of contact with the keeper notch 215 when opening or detaching the facepiece assemblies 400A-400D.

It is also possible to see the sealing facepiece flange 209 of the oronasal mask 206 in between the cartridge facepiece body 401 and the frame body 201 and full-face lens 202. As the facepiece flange 209 is thicker than the gap between the cartridge facepiece body 401 and frame body 201 and full-face lens 202, the pressure placed upon the outer sealing faces 204 of the facepiece flange 209 provides a positive seal for the respirator as unit while the resistive force of the squeezed flexible material keeps the over center latch 405 and keeper bar 404 in tension to ensure a positive lock.

Figure 14:
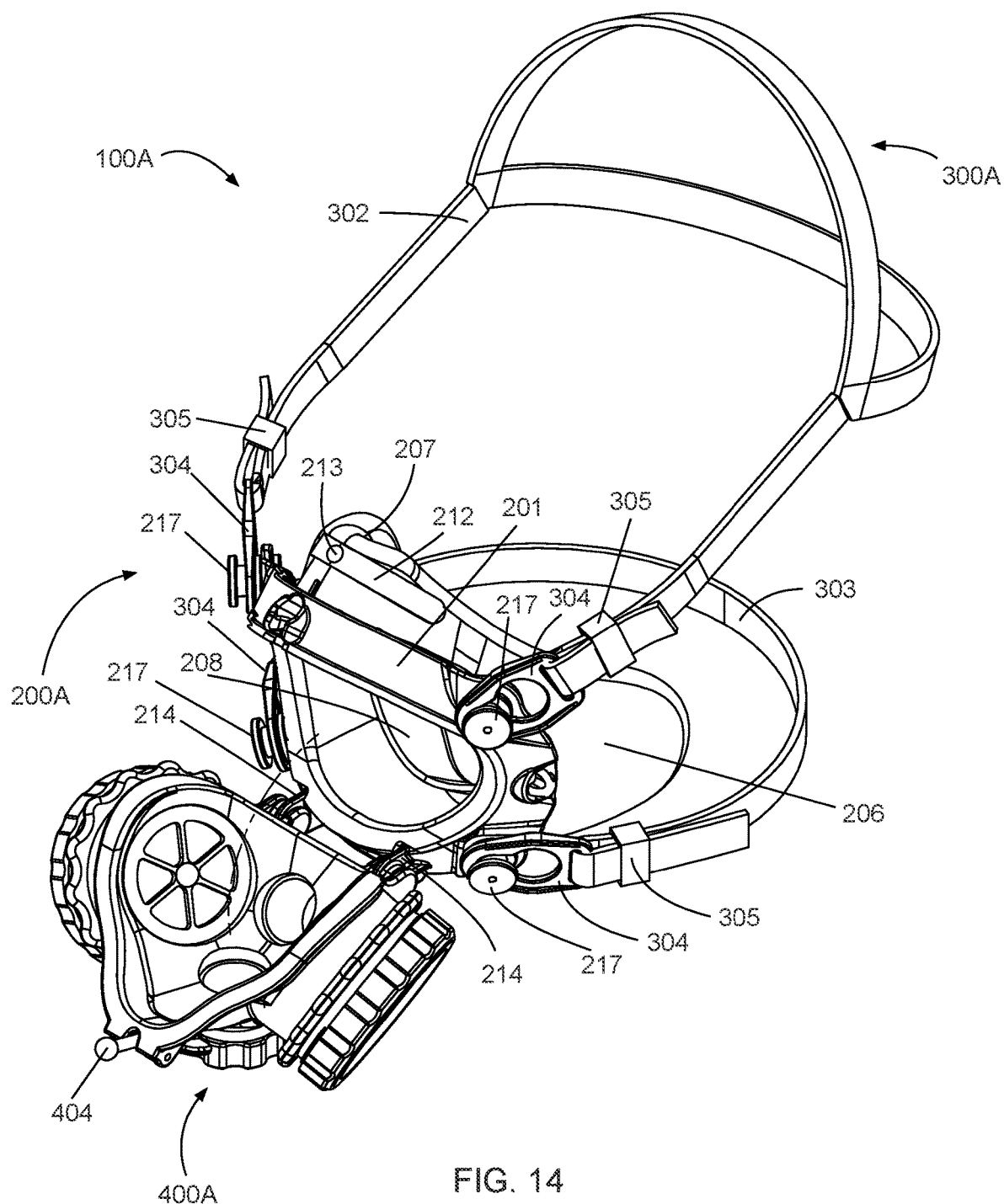
FIG. 14 is an alternative perspective view of a half-face respirator 100A, where the facepiece assembly is shown in an open and attached position, in accordance with an embodiment.
Figure 15:
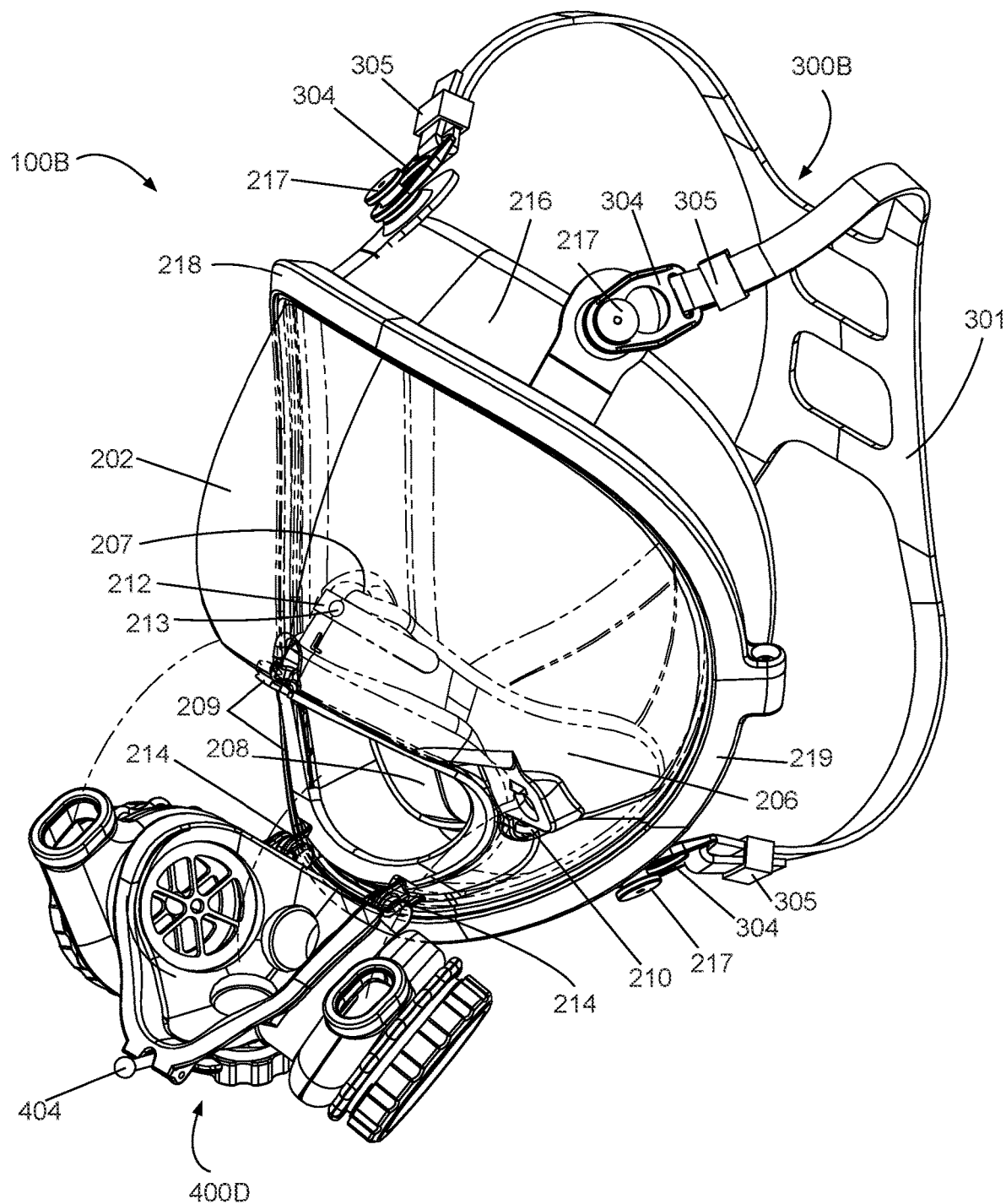
FIG. 15 is an alternative perspective view of a full-face respirator 100B, where the adapted cartridge facepiece assembly 400D is shown in an open and attached position, in accordance with an embodiment.

FIGS. 14 and 15 illustrate both the half-face respirator 100A and full-face respirator 100B in perspective views with their facepiece assemblies in an open, yet captive position. Specifically, FIG. 14 illustrates how the cartridge facepiece assembly 400A with its intake filter cartridge 500A and exhaust filter cartridge 500B may hinge open in accordance with one embodiment of the present disclosure. FIG. 15 similarly shows its adapted cartridge facepiece assembly 400D in an open yet captive position for a full-face configuration. More clearly visible in these views is the sealing oronasal flange 208 through the oronasal opening 203, as well as the annular hinge knuckles as they interface with a facepiece assembly. The securing and opening benefits as partially illustrated in FIGS. 14 and 15 allow the wearer to perform activities such as eating, take medicine, or talking on a phone. This is made possible by the annular hinge knuckles 214 of the frame body 201 and full-face lens 202 and hinge pins 406 on the cartridge facepiece body 401 which are more visible in FIGS. 18 to 26. With the ventilator-adaptive facepiece assembly 400C shown in FIGS. 24-26, this would permit hospital staff to check and clean the nose and mouth regions of an intubated patient.

Figure 16:
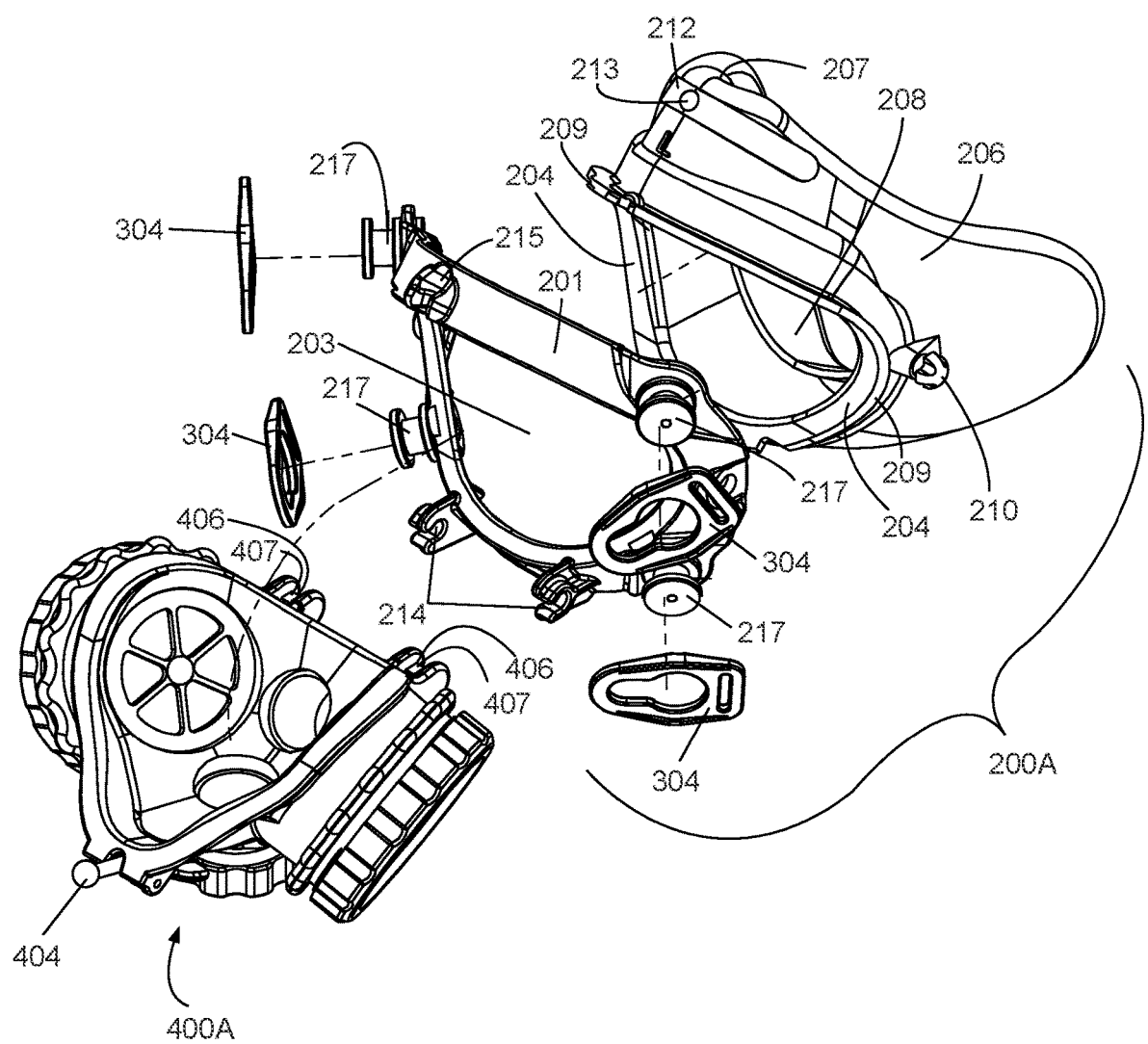
FIG. 16 is an exploded view of the half-face assembly 200A with a cartridge facepiece assembly 400A, in accordance with an embodiment.
Figure 17:
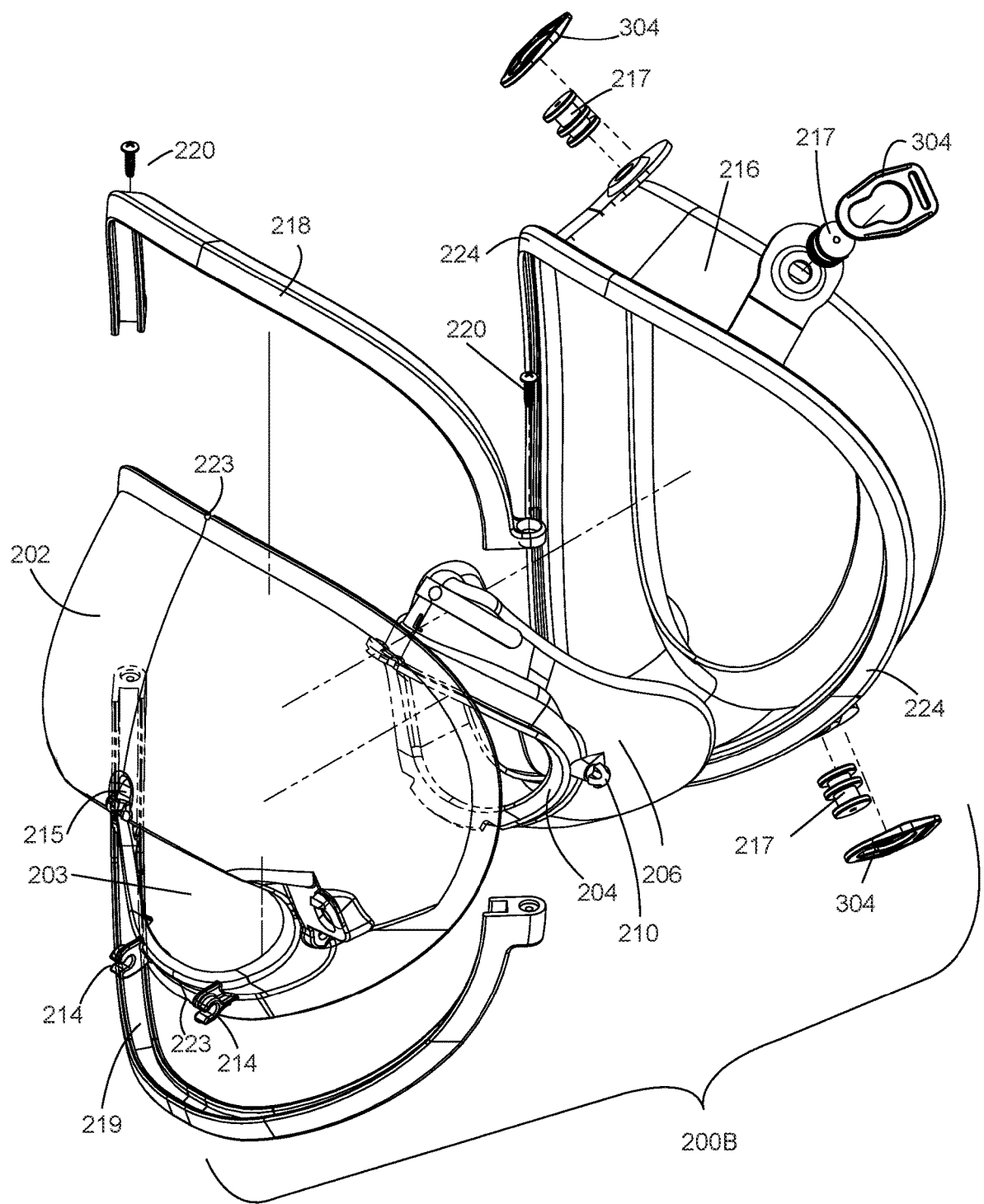
FIG. 17 is an exploded view of the full-face assembly 200B, in accordance with an embodiment.

FIGS. 16 and 17 show partial exploded views of the respirators shown in FIGS. 14 and 15. In FIG. 16, the sealing faces 204 of the facepiece flange 209 on the oronasal mask 206 are visible, as is the sealing oronasal flange 208 and the oronasal mounting stem 210 that provides a secure fit to either a frame body 201 or full-face lens 202. Also visible are the annular hinge knuckles 214 and the corresponding pins 406 of the facepiece assemblies along with flats 407. In this instance, the two-part harness attachment elements 217 that the buckles 304 attach to are securely fastened to the frame body 201.

The exploded view in FIG. 17 shows the full-face assembly 200B. As can be seen therein, the annular hinge knuckles 214 are a part of the full-face lens 202. The oronasal mask 206 fits through the oronasal opening 203 and is secured to the full-face lens 202 via the oronasal mounting stem 210. Over and to the outside of the oronasal mask 206 goes the face seal 216, whose face mask sealing flange 224 fits onto the outer edges of the full-face lens 202, is aligned by alignment notches 223 on the full-face lens 202, and is retained by an upper lens keeper 218 and a lower lens keeper 219. The procedure to secure the face seal 216 to the full-face lens 202 makes the upper lens keeper 218 and lower lens keeper 219 slide over the combined lens and seal in a manner well known to respirators, where securing fasteners 220 fasten the components together. Referring to FIG. 14, the two-part harness attachment elements 217 are shown assembled as a single unit, and then placed in the holes of the face seal 216 for the harness buckles 304 to mount. This promotes further part compatibility across the respirator configurations of the present disclosure.

Figure 18:
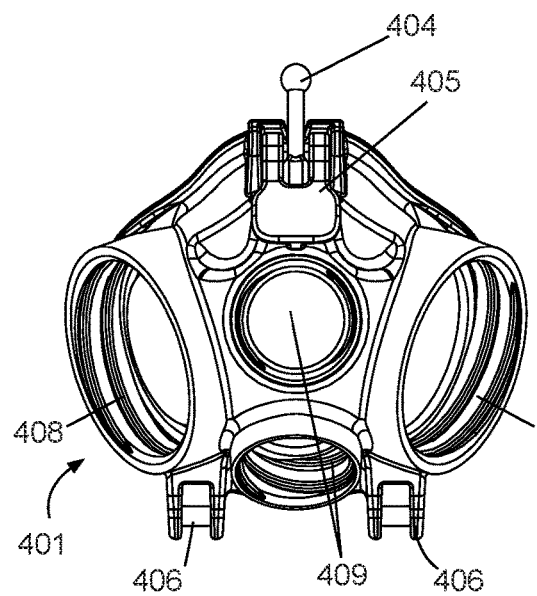
FIG. 18 is a front view of a cartridge facepiece assembly 400A, in accordance with an embodiment.
Figure 19:
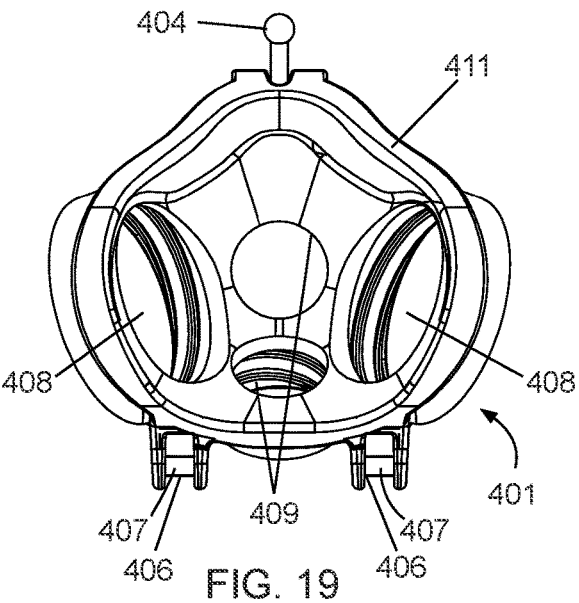
FIG. 19 is a rear view of the cartridge facepiece assembly 400A shown in FIG. 18.
Figure 20:
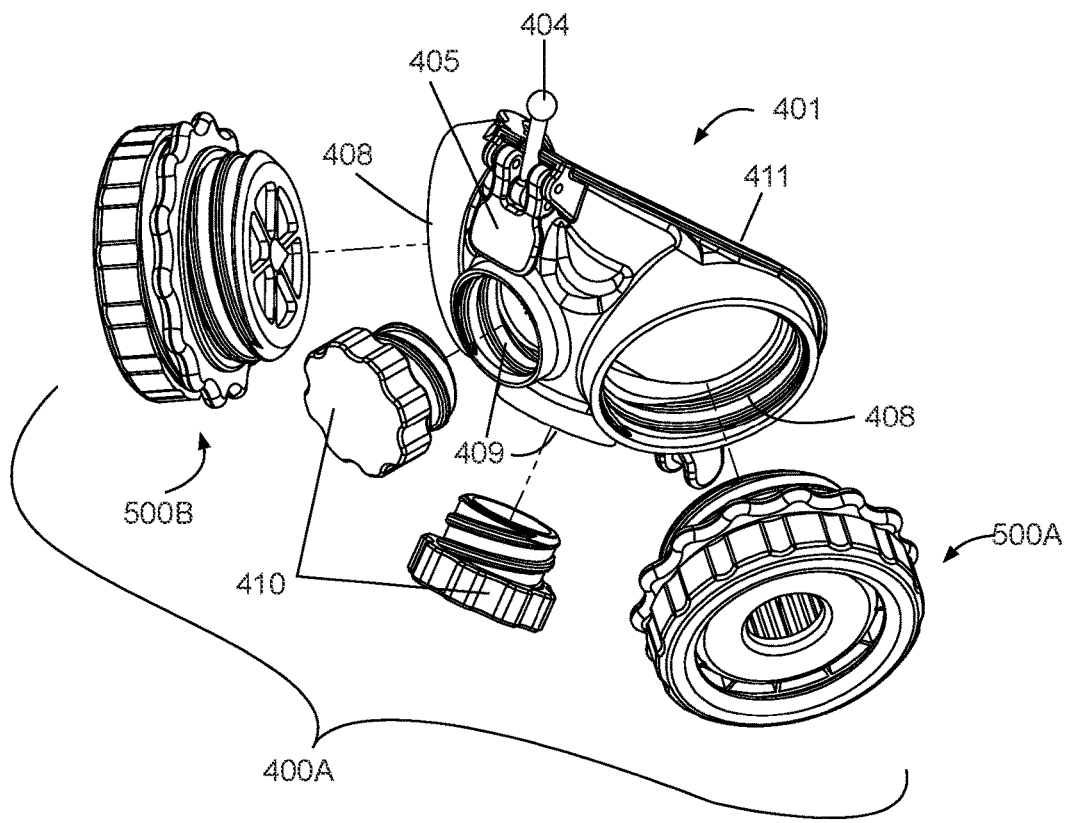
FIG. 20 is an exploded view of the cartridge facepiece assembly 400A shown in FIG. 18 with filter cartridge assemblies 500A and 500B, in accordance with an embodiment.

While the functionality of the facepiece embodiments differs in their application, there is a significant degree of shared features between the various assemblies. FIGS. 18 and 19 show a cartridge facepiece 400A in a front view and rear view respectively, while FIG. 20 shows an exploded view of a cartridge facepiece assembly with accessory plugs 410 and intake filter cartridge 500A and exhaust filter cartridge 500B. FIGS. 18 and 19 show cartridge ports 408 disposed on the left and right sides of the cartridge facepiece body 401, along with a facepiece sealing surface 411. Located medially on the faceplate 401 are the accessory ports 409. The top accessory port 409 may accept at least one of an insert comprising at least a microphone and speaker device; an insert with lid and flexible medium with flaps through which a medical device such as an inhaler may be inserted; an insert with a flashlight and battery; or an accessory plug 410 to close off the port 409. The lower accessory port 409 may accept at least one of an insert with lid and flexible medium with flaps through which a straw may be inserted for the wearer to drink, and an accessory plug 410 to close off the port 409. This facepiece embodiment provides the wearer a great deal of flexibility in its use applications while also providing multiple means of changing out filters that have become saturated or compromised.

FIGS. 21 and 22 show the negative-pressure filter facepiece assembly 400B in front and rear views, respectively, while FIG. 23 shows an exploded view of a negative-pressure filter facepiece assembly 400B with a filter medium 413 and a filter frame 414. A breathing port 415 is disposed in the non-cartridge facepiece body 402 and serves as both intake and exhaust ports, through which air from the external environment passes through the filter medium 413 into the interior gas space of the mask. The filter medium 413 is supported by a frame 414 that holds the filter medium 413 away from the wearer's face. Further, the frame 414 sits flush with the rearward face of the non-cartridge facepiece body 402 and helps form the seal between the filter medium 413 and the frame assembly being used. This embodiment would be ideal for the majority of everyday use applications, as the filter medium may comprise a material ranging from simple fabric through mediums rated to N95 standards and above.

Figure 24:
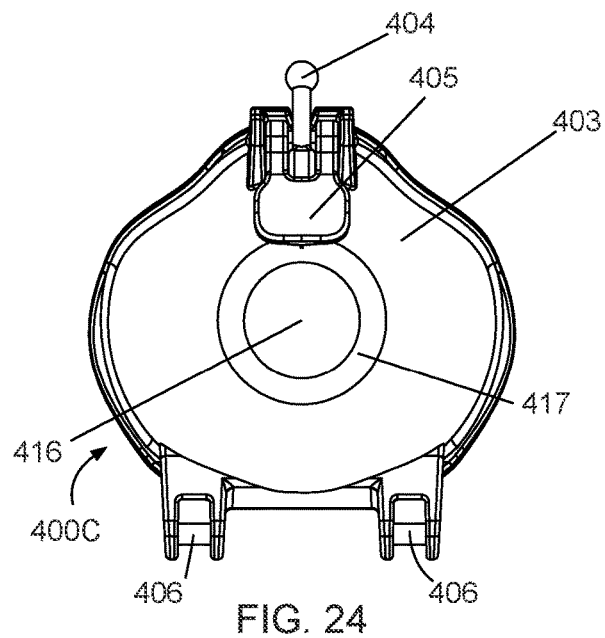
FIG. 24 is a front view of a ventilator-adaptive facepiece assembly 400C, in accordance with an embodiment.
Figure 25:
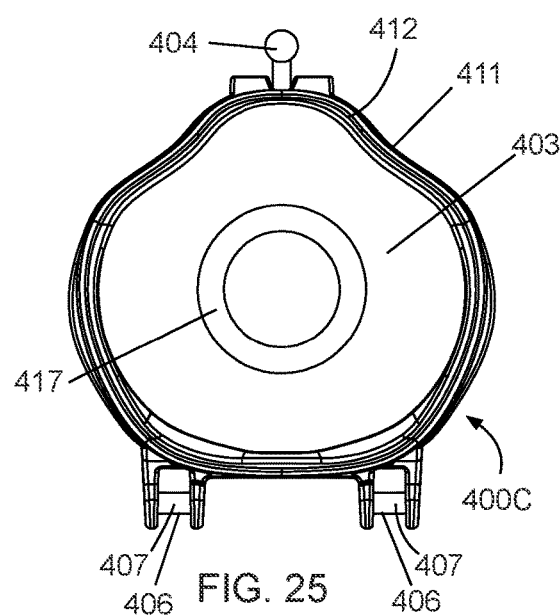
FIG. 25 is a rear view of the ventilator-adaptive facepiece assembly 400C shown in FIG. 24.
Figure 26:
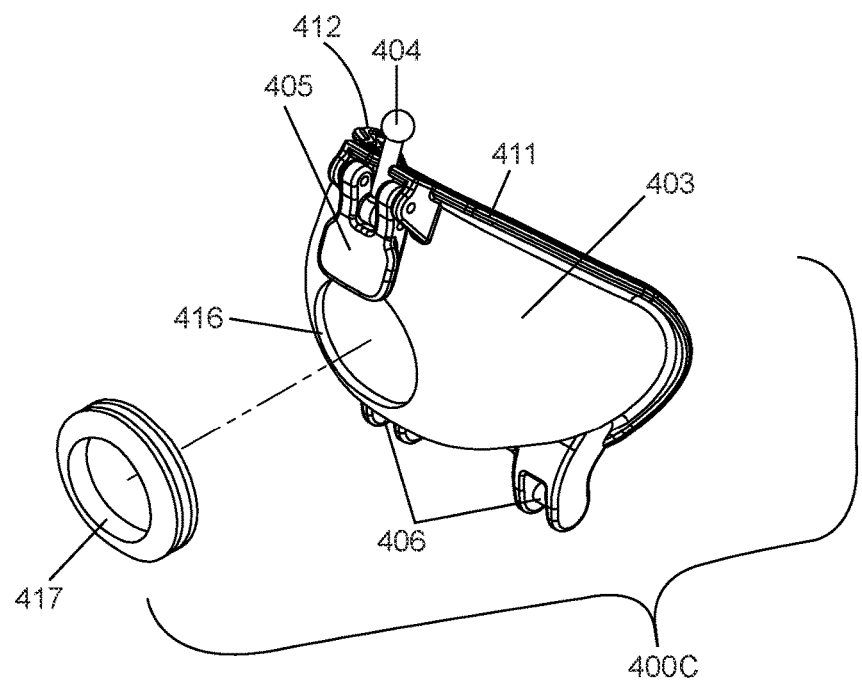
FIG. 26 is an exploded view of the ventilator-adaptive facepiece assembly 400C shown in FIG. 24.

FIGS. 24 and 25 show the ventilator-adaptive facepiece assembly 400C in front and rear views respectively, with FIG. 26 showing an exploded view of the ventilator-adaptive facepiece assembly 400C with a port 416 and a sealing grommet 417. Unlike the cartridge facepiece assembly 400A and negative-pressure filter facepiece 400B, the ventilator-adaptive facepiece body 403 has one port 416 rimmed with the sealing grommet 417. The port 416 and grommet 417 may be sized to accept the hose ends of ambu bags and the intubation tubes for mechanical ventilators. This allows the wearer/patient to have the mechanical ventilation they need for respiration, while sealing off their nose from the external environment. This is a paramount advantage in the case of infectious disease treatment, as an intubated patient may still exhale through their nose. By sealing off the nose within the interior gas space of the respirator via the frame and mask assemblies and the grommet 417, the patient will still be able to breathe through the devices attached to the ventilator-adaptive facepiece body 403.

Shared between facepiece assemblies 400A-400C illustrated in FIGS. 18 through 26 are the over center latch 405 with the keeper bar 404, and the hinge pins 406 with the flats 407. In accordance with a preferred embodiment, a gasket rib 412 along the facepiece sealing surface 411 may be used to ensure a positive seal against the facepiece flange 209 of the oronasal mask 206. The standardization of the common parts 100C (again, which comprise the facepiece assemblies 400A-400D and the oronasal mask 206 with its multiple features) ensures more than one or all facepiece embodiments may be exchanged or hot-swapped for one another regardless of individual wearer's size or the configuration of respirator being worn. This is of significant advantage when filtering elements become wet or contaminated, as it can reduce the time needed to exchange those filtering elements and ensures universal fit to the frame assemblies. As an example, should a patient who was wearing the present respirator with a cartridge facepiece assembly 400A or a negative-pressure filter facepiece assembly 400B be admitted to the hospital or picked up by an ambulance, the related staff need only undo the over center latch 405 and the keeper bar 404 to remove the in-use facepiece assembly and replace it with the ventilator-adaptive facepiece assembly 400C. The flats 407 on the hinge pins 406 are common across the facepiece bodies are included to limit the facepiece assembly to be removed from the annular hinge knuckle 214 of a frame body 201 or full-face lens 202 by rotating it sufficiently that the flat 407 clears the knuckle 214. It is believed that this feature will aid in reducing the number of unintentional facepiece separations a wearer may experience when opening the facepiece assembly to talk, eat, or exchange for another facepiece assembly.

Figure 27A:
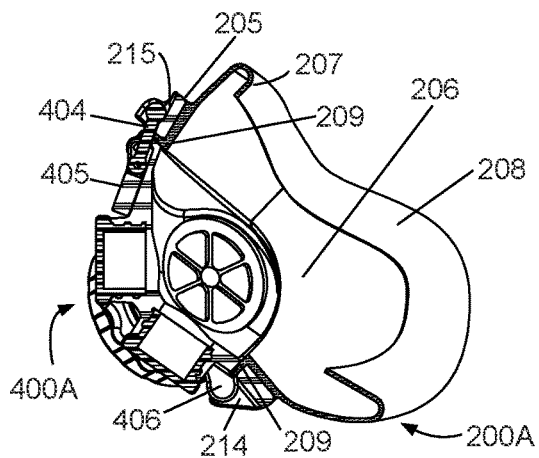
FIG. 27a through FIG. 27e illustrate the facepiece securing and disengaging procedure according to an embodiment.
Figure 27B:
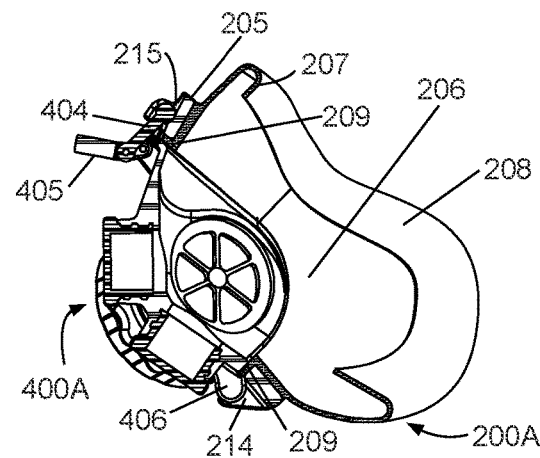
Figure 27C:
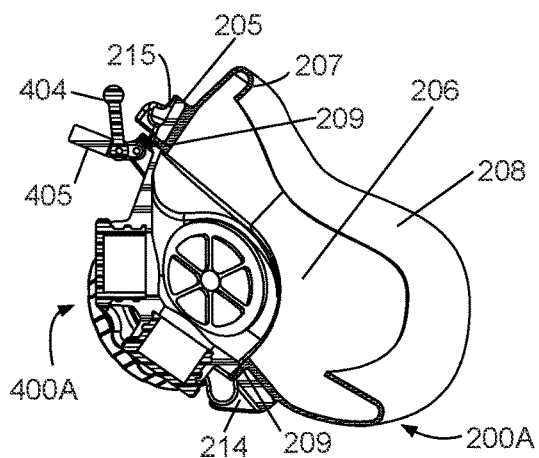
Figure 27D:
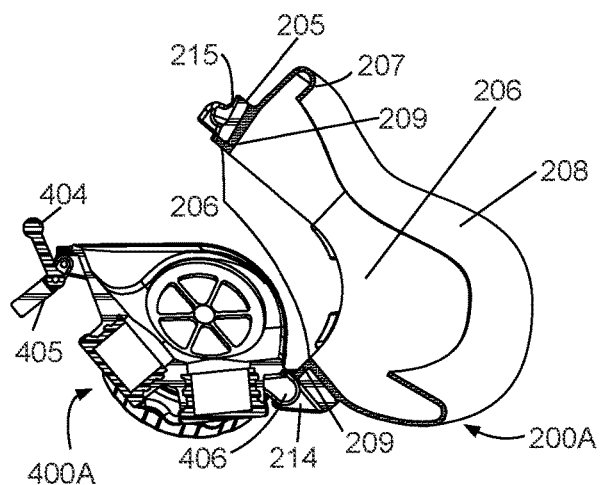
Figure 27E:
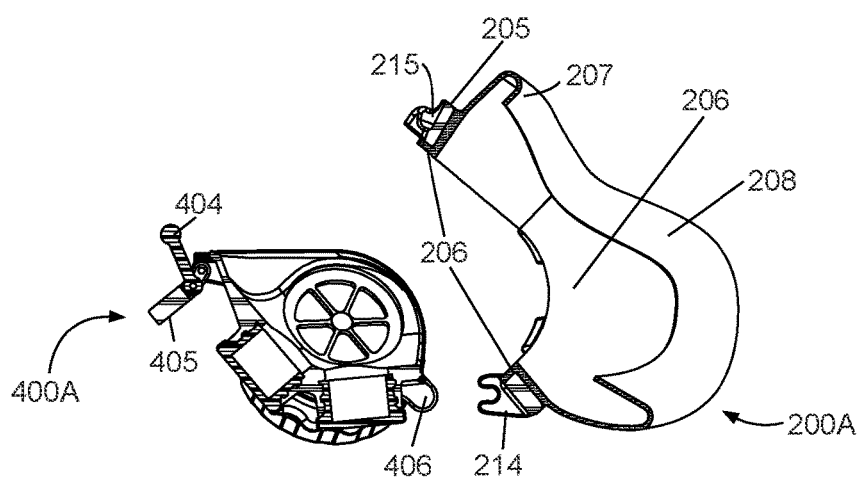

Illustrating the procedure for unlocking and detaching the facepiece assemblies 400A/400B from the frame, FIGS. 27a through 27e show cross-sectional views of the half-face assembly 200A with cartridge facepiece assembly 400A to better show some of the features of the present disclosure, although this applies to all frame and facepiece embodiments. Visible in these views are the nose contour notch 207 of the ventilator-adaptive facepiece assembly 400C, the sealing oronasal flange 208, and the sealing facepiece flange 209 of the flexible mask body 206, as well as the keeper notch 215 at the top of the frame body 201. Located towards the bottom are the annular hinge knuckles 214 on the frame body 201 and the hinge pins 406 on the facepiece: these two hinge features form the axis around which the facepiece assemblies 400A-400D rotate. FIG. 27a shows respirator in a closed and locked position. To begin unlocking the facepiece, rotate the over center latch 405 upward, as shown in FIG. 27b. As shown in FIG. 27c, this will remove the tension on the keeper bar 404 and permit the wearer to rotate the keeper bar 404 out of the keeper notch 215. Doing so will then permit the facepiece assemblies 400A-400D to rotate about the hinge pins 406 in the annular hinge knuckles 214 as seen in FIG. 27c. Finally, as illustrated in FIG. 27d, as the knuckles 214 are not fully enclosed, rotating the facepiece assemblies 400A-400D so that the flats 407 of the facepiece pins 406 are aligned with the end of the annular hinge knuckle 214, the facepiece assemblies 400A-400D can then be pulled out of the annular hinge knuckles 214 to detach the facepiece. This procedure for opening, retaining, and exchanging facepiece assemblies 400A-400D is shared across the half-face 100A and full-face 100B respirator configurations of the present disclosure.

Figure 28:
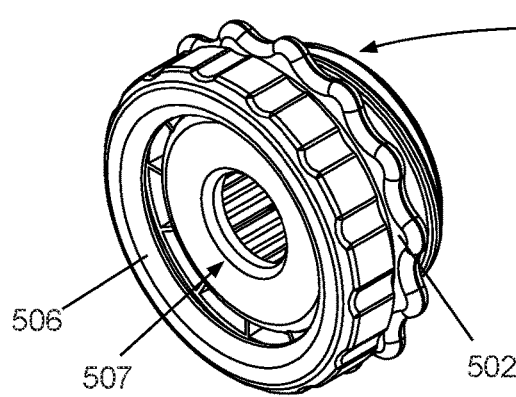
FIG. 28 is a front perspective view of a filter cartridge assembly in an exhaust configuration 500B, in accordance with an embodiment.
Figure 29:
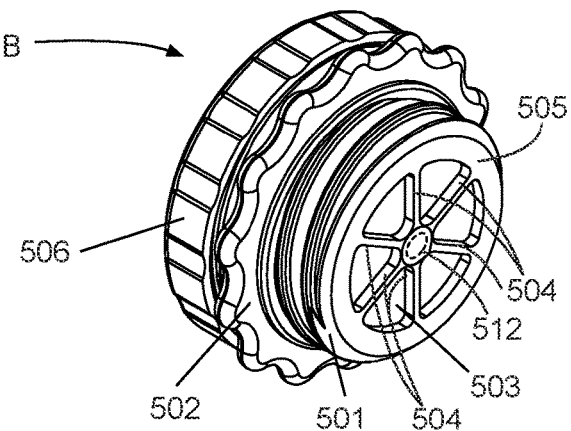
FIG. 29 is a rear perspective view of the filter cartridge assembly of FIG. 28.
Figure 30:
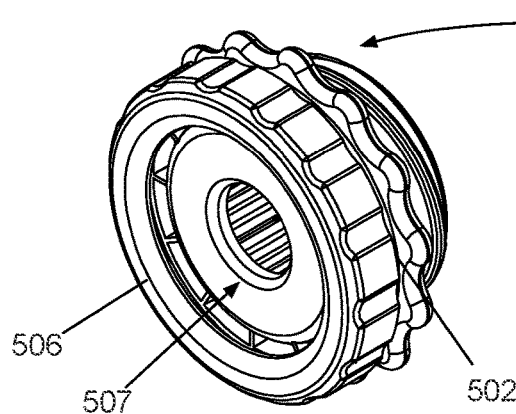
FIG. 30 is a front perspective view of a filter cartridge assembly in an intake configuration 500A, in accordance with an embodiment.
Figure 31:
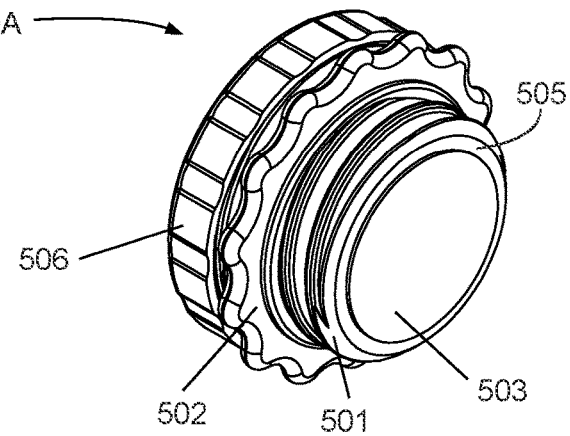
FIG. 31 is a rear perspective view of the filter cartridge assembly of FIG. 30.
Figure 32:
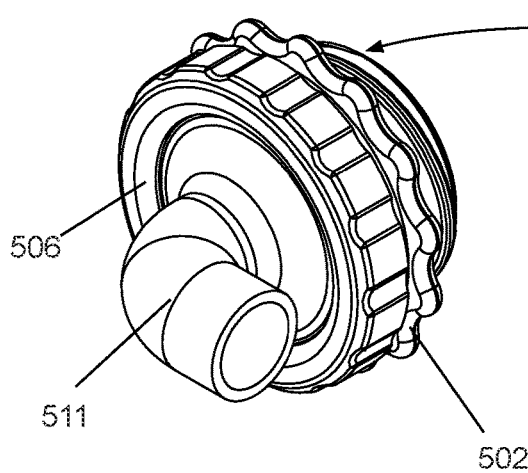
FIG. 32 is a front perspective view of a filter cartridge assembly in an intake configuration 500A with a positive air adapter 511, in accordance with an embodiment.
Figure 33:
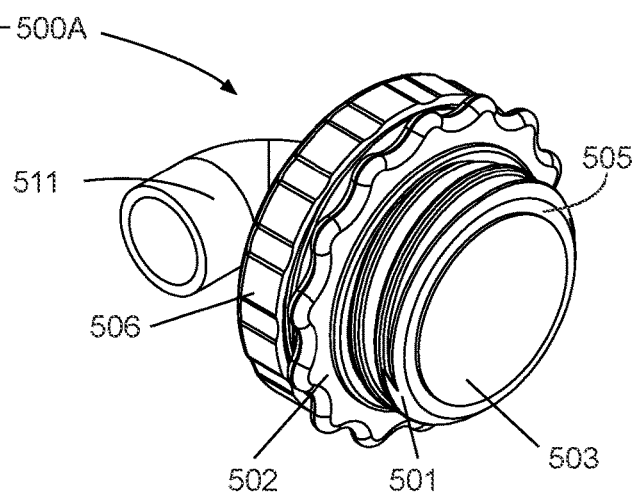
FIG. 33 is a rear perspective view of the intake configuration 500A and positive air adapter 511 of FIG. 32.

Turning to the filter cartridges 500A/500B for filtering air to create clean air for the wearer that may be utilized with the cartridge facepiece assembly 400A, FIGS. 28 and 29 show front and rear perspective views, respectively, of the exhaust filter cartridge 500B, while FIGS. 30 through 33 show intake filter cartridges 500A in similar views. The filter cartridges 500A/500B may be configured to releasably secure and releasably resecure with the facepiece assembly 400A. Specific to FIGS. 30 and 31, a positive air adapter 511 is shown as part of the cartridge facepiece assembly 400A for use with powered air-purifying respirators units. The adapter 511 may be in gaseous disposed and in gaseous communication between the cartridge facepiece body 401, an intake filter cartridge 500A, and an exhaust filter cartridge 500B. Visible in these drawings are a filter retaining ring 506 that secures a filter element 507 into the cartridge assembly by fastening the filter retaining ring 506 with the filter element 507 onto the cartridge body 501. As shown in FIGS. 32 and 33, the retaining ring 506 may further fasten upon the positive air adapter 511 and the filter element 507 to create a positive seal. A grip ring 502 may either be over-molded onto or be made an integral part of the cartridge body 501 in accordance with some embodiments. Further, the grip ring 502 may be colored coded to aid in visual identification of the filter cartridge as either an intake cartridge 500A or an exhaust cartridge 500B. One or more of the face assembly 200A, the facepiece assembly 400A, or the securing headgear 300A may be configured to be released from the respirator, sterilized, and releasably resecured with the respirator 100A.

According to some embodiments, a check valve 503 may be configured on the cartridge body 501 to ensure the uni-directional flow of air through the cartridge. When placed on the outside of the cartridge body 501 as illustrated in FIGS. 30-33, the unit is configured as the intake filter cartridge 500A. In this configuration, the wearer may draw air from the external environment through the filter element 507 and past the check valve 503 into the interior gas space of the respirator. FIGS. 28-29 shows with the check valve 503 are positioned inside the cartridge body 501 so the unit becomes the exhaust filter cartridge 500B. Set up in this way, exhaled air may pass from the interior gas space past the check valve 503 through the filter element 507 and out into the external environment. This setup of sealed filter mediums and check valves ensures that inhaled air taken into the respirator and exhaled air exhausted from the respirator are filtered, and the only ingress points to the interior gas space of the respirator are through the filter elements 507. As previously described, the check valve 503 is removable for either reconfiguration or cleaning.

As seen in FIGS. 32-33, to facilitate the use of powered air-purifying respirators (PAPR) units and other mechanical ventilator units such as CPAP and BiPAP units, it is possible to place the positive air adapter 511 between the retaining ring 506 and the filter element 507 so the wearer may attach standardized hose and oxygen supplying fittings.

Figure 34:
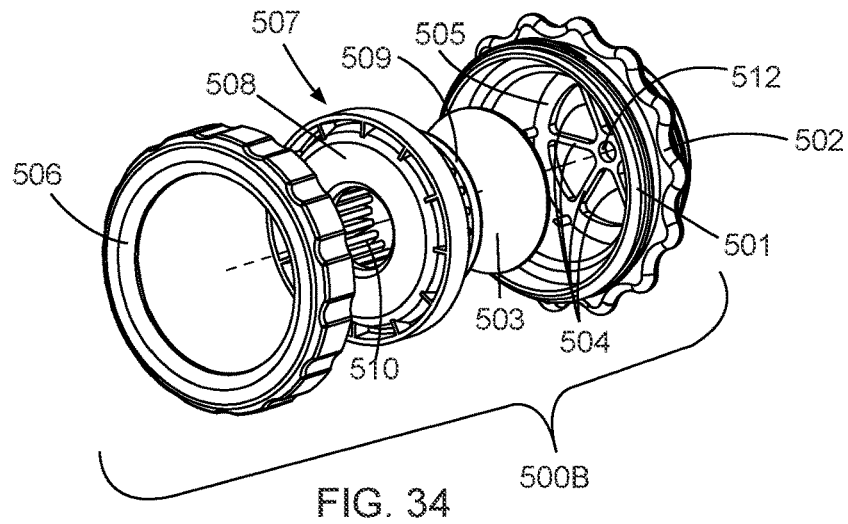
FIG. 34 is an exploded view of an exhaust filter cartridge assembly 500B, in accordance with an embodiment.
Figure 35:
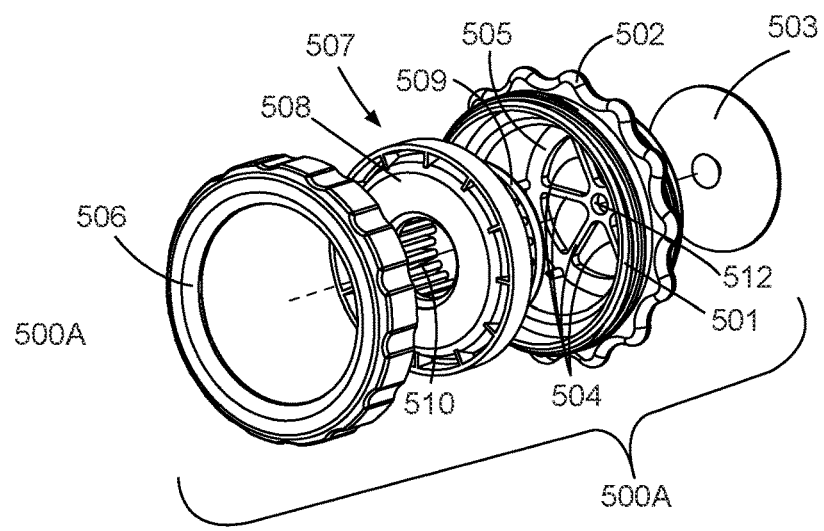
FIG. 35 is an exploded view of an intake filter cartridge assembly 500A, in accordance with an embodiment.
Figure 36:
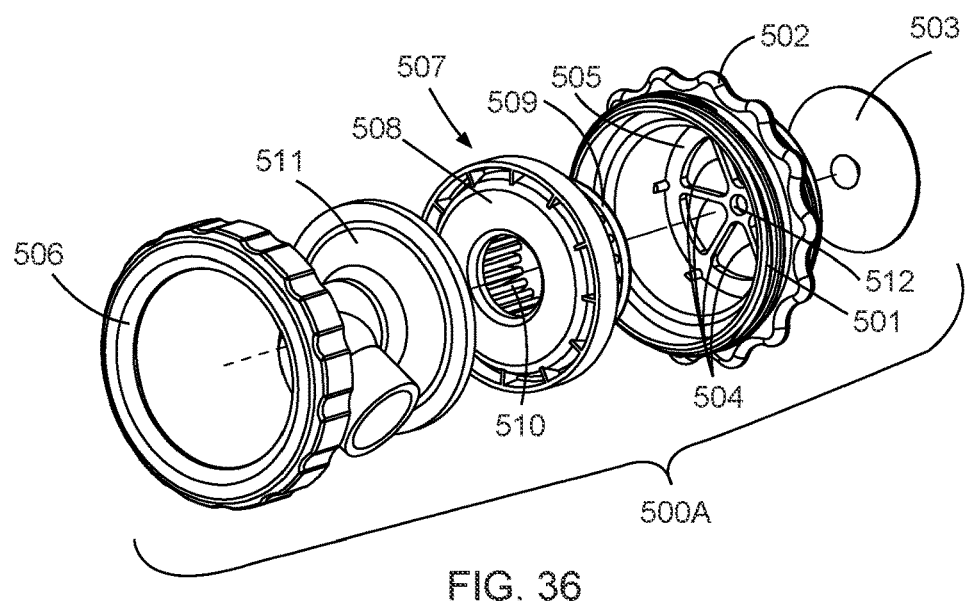
FIG. 36 is an exploded view of an intake filter cartridge assembly 500A with positive air adapter 511, in accordance with an embodiment.

To better illustrate the various cartridge embodiments, FIGS. 34 through 36 show exploded views of the filter cartridges 500A/500B. It is also possible to see the components that make up the filter element 507 according to one embodiment: the upper member 508 and lower member 509 which may be made of a resilient elastomeric material, and the filter material 510 itself. It is the upper member 508 that the retaining ring 506 cams against when fastening to the cartridge body 501 to create an airtight seal. FIG. 34 shows the exploded exhaust filter cartridge 500B, with a retaining ring 506 fastening at least one of the filter element 507 into the cartridge body 501 with the grip ring 502. The check valve 503 is positioned inside of the cartridge body 501 through a central port 512, (shown in FIG. 29), of a valve structure 504 (shown in FIG. 29) and sits against a valve seat surface 505. FIGS. 35 and 36 show intake filter cartridges 500A where the check valve 503 is place on the outer face of the cartridge body 501. Finally, as shown in FIG. 36 and if desired, the positive air adapter 511 may be fastened against the filter element 507 via the retaining ring 506 so powered air-purifying filters and other assistive breathing devices may be utilized by the wearer.

Figure 37:
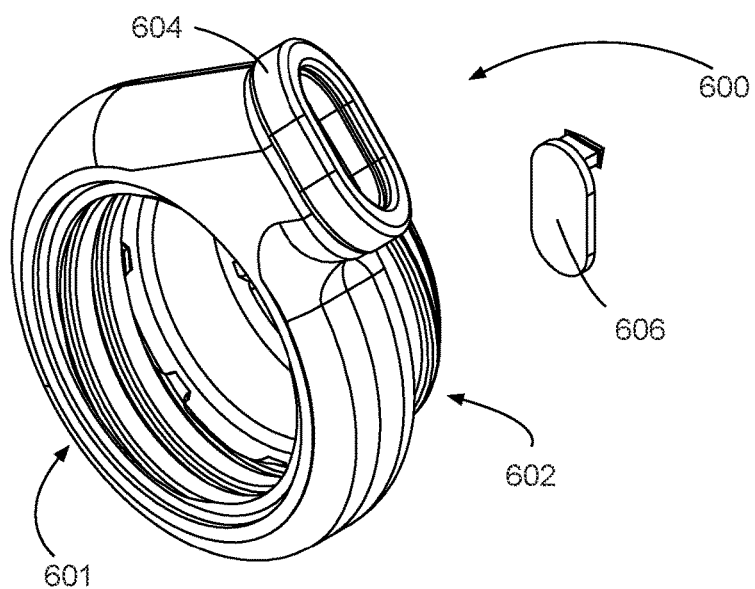
FIG. 37 is a perspective view of the full-face adapter assembly 600 (referred to as "adapter assembly"), in accordance with an embodiment.
Figure 38:
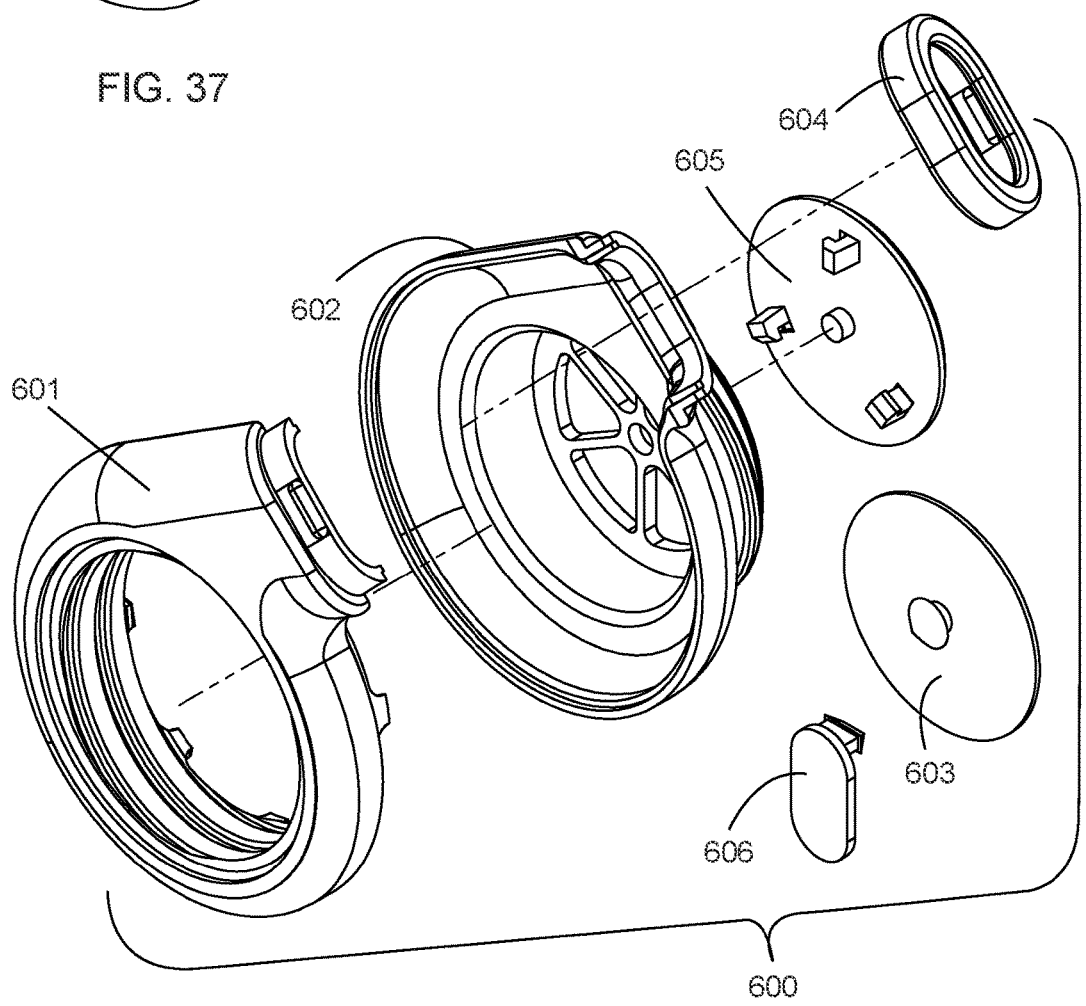
FIG. 38 is an exploded view of the adapter assembly 600, in accordance with an embodiment.
Figure 39:
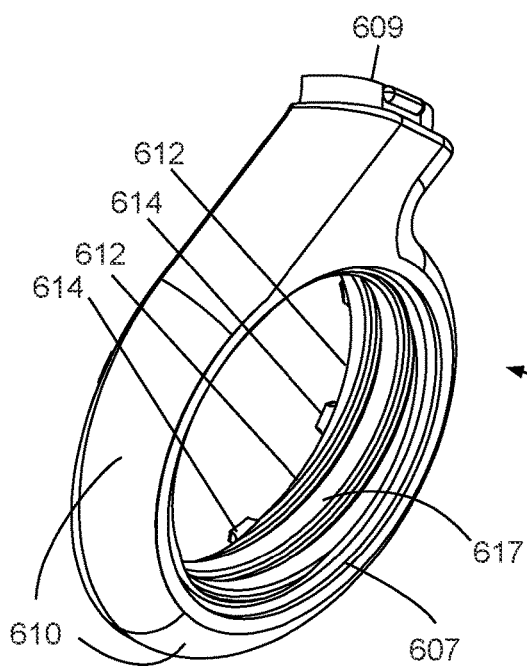
FIGS. 39 and 40 show the cartridge side housing 601 of the adapter assembly 600 in a front and rear perspective view, respectively, in accordance with an embodiment.
Figure 40:
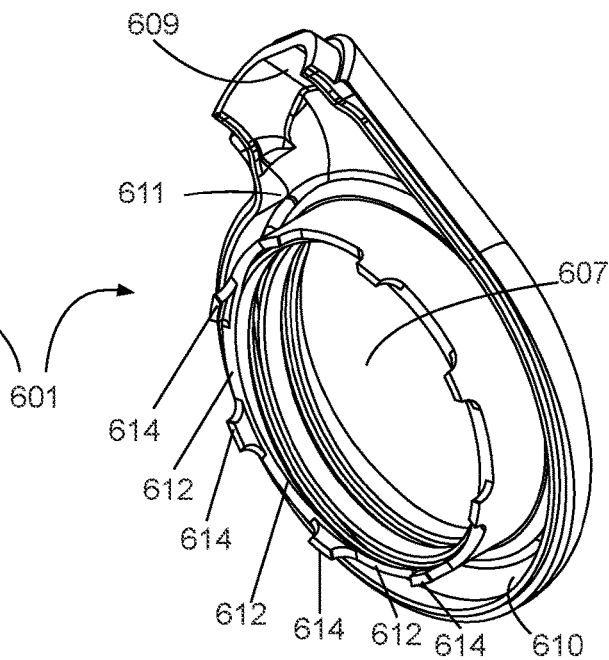
Figure 41:
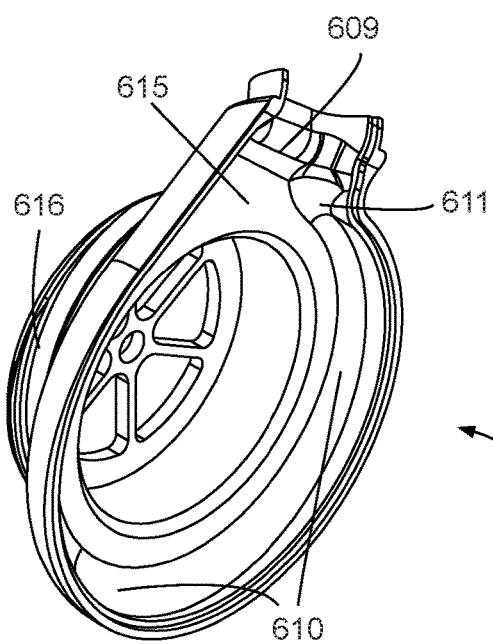
FIGS. 41 and 42 show the respirator side housing 602 of the adapter assembly 600 in a front and rear perspective view, respectively, in accordance with an embodiment.
Figure 42:
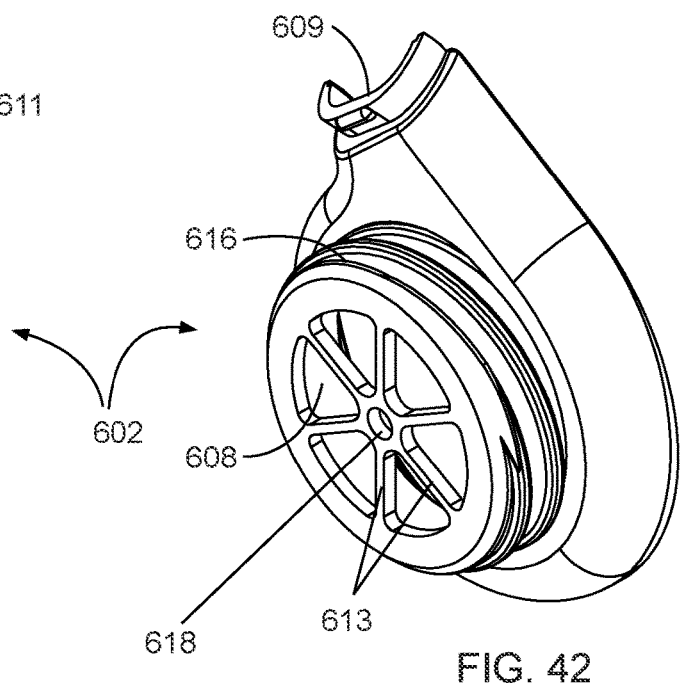

FIGS. 28 through 36 illustrate the filter cartridges 500A/500B as would be used by the half-face respirator 100A, but for use in a full-face configuration according to the present disclosure, the adapter assembly 600 is required. FIG. 37 shows the adapter assembly 600 in its assembled state with its core components: a cartridge-side body 601, a respirator-side body 602, an adapter gasket 604, and one or more anti-fog check valves 606 that is used with the full-face lens 202. The one or more anti-fog check valves 606 may be configured to direct a flow of air into, through, and out of the interior gas space. As shown in the exploded view of FIG. 38, a flow restrictor 605 and a check valve 603 (which can advantageously be the same check valve as that of 503) for configuring the adapter assembly 600 according to its cartridge fastening means. FIGS. 39 and 40 illustrate the cartridge-side body 601 in front and rear perspective views, respectively, while FIGS. 41 and 42 show the respirator-side body 602 in similar front and rear perspective views, respectively.

In accordance with some embodiments, the cartridge-side body 601 and respirator-side body 602 may incorporate a volute-type collection region 610 in an effort to maintain the speed and rate of airflow through the full-face respirator 100B. Both bodies 601 and 602 may comprise a volute-tongue 611 to help maintain and regulate the flow of air through the interior of the adapter assembly 600, and at the end of the bodies 601 and 602 is located a volute nozzle 609 from which cleaned air will pass to and from the filter cartridges 500A/500B. According to specific embodiments where the filter cartridges are of the threaded type, the cartridge-side body 601 comprises a cartridge-side port 607 that incorporates interior threads 617 in order to fasten and secure the filter cartridges. At the base of the cartridge-side port 607 are vent cuts 612 through which air can pass through. The entire assembly is kept from collapsing by the stand-offs 614 which meet the respirator-side interior shoulder 615. On the respirator-side body 602 is a respirator-side port 608, which in the embodiment shown in FIGS. 41-42 takes a threaded form 616 similar to the cartridge body 501. Also like those of the cartridge body 501 are the open framework 613 and an axial aperture 618. In FIGS. 43a through 44b, the asymmetric nature of the volute-collector form 610 previously illustrated in FIGS. 39-42 can be more readily noted, as are the vent cuts 612 with their stand-off supports 614 that will meet the respirator-side interior shoulder 615 when assembled.

Figure 45:
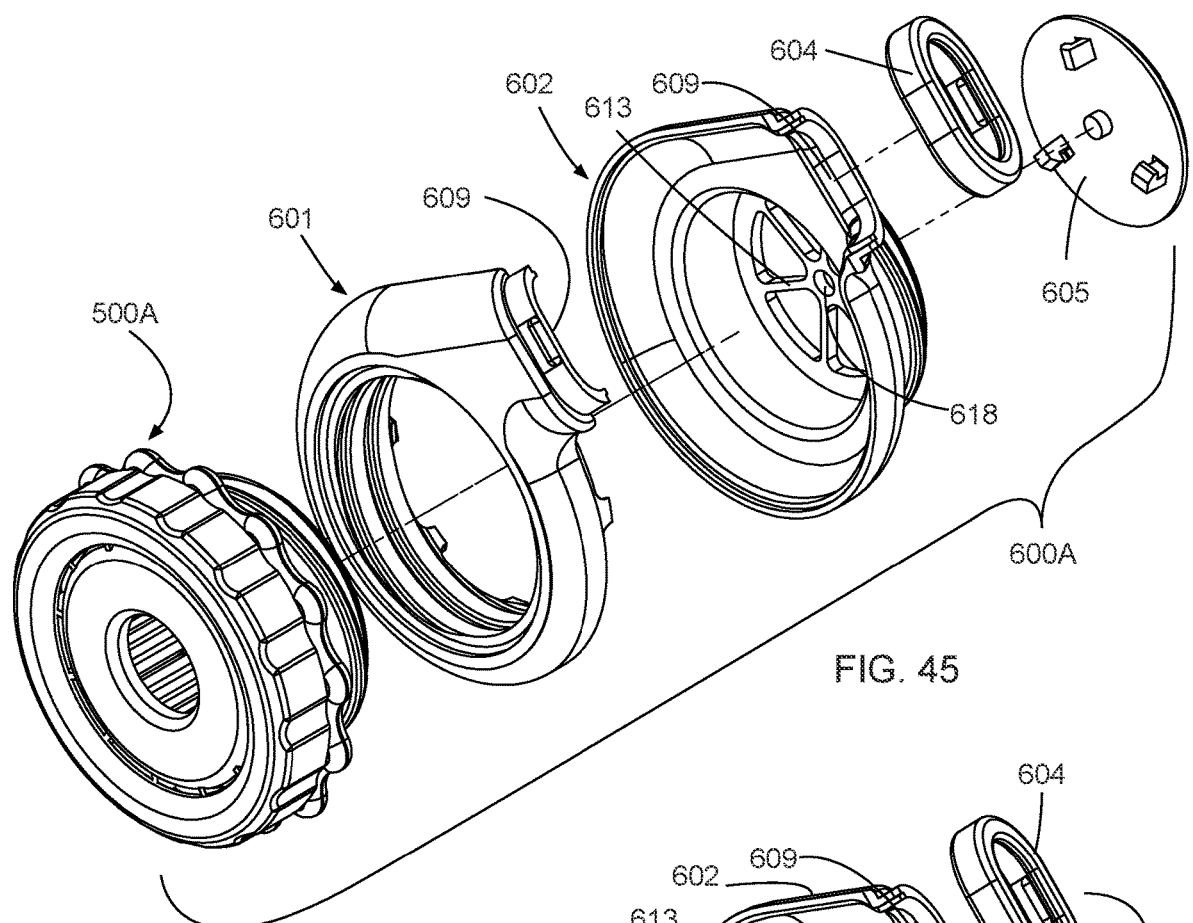
FIG. 45 is an exploded view of a threaded adapter assembly 600A, in accordance with an embodiment.
Figure 46:
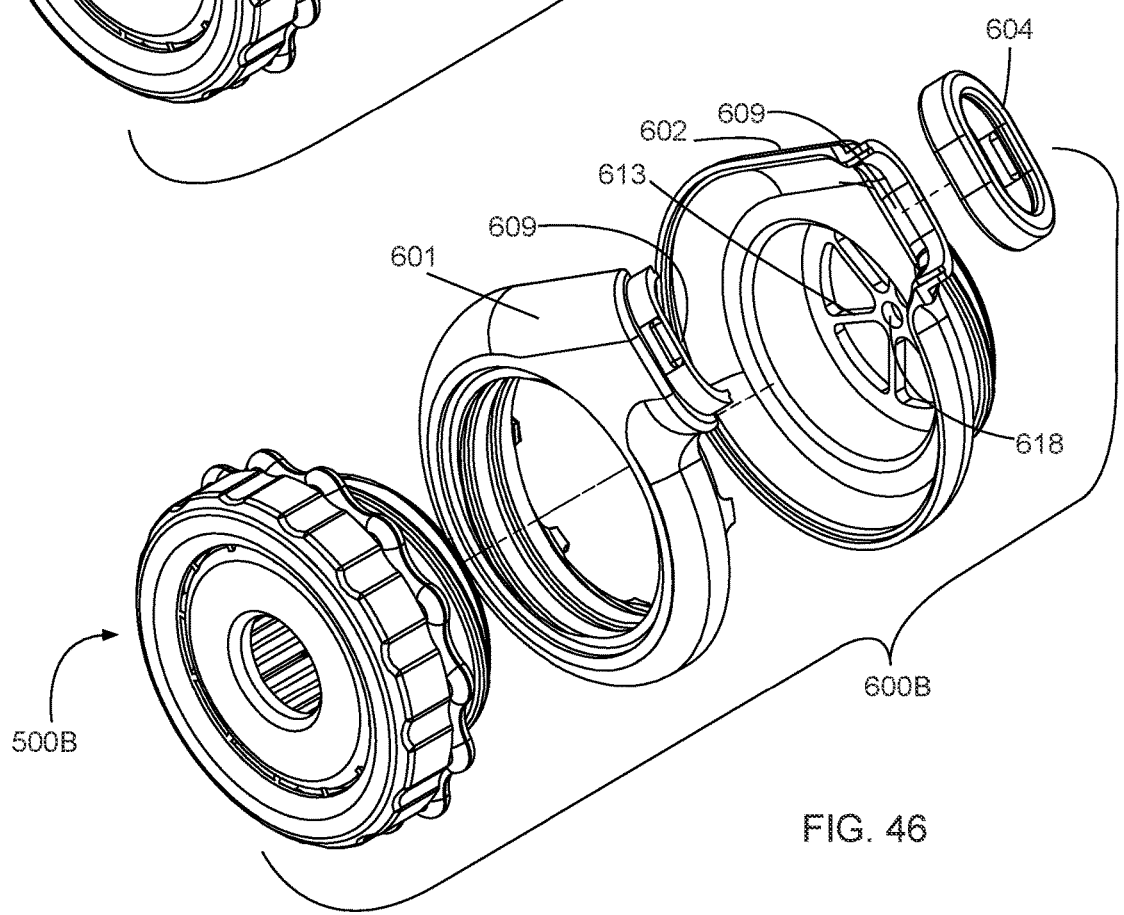
FIG. 46 is an exploded view of a threaded exhaust adapter assembly 600B, in accordance with an embodiment.

FIGS. 45 and 46 illustrate exploded views of the adapter assembly 600. Specifically, FIG. 45 shows a threaded intake adapter assembly 600A with intake filter cartridge 500A and an airflow restrictor 605 that align with the axial aperture 618 and secures to the open framework 613 of the respirator-side body 602. With the threaded exhaust adapter 600B and exhaust filter cartridge 500B shown in FIG. 46, no flow restrictor 605 is utilized because of the bi-directional flow of air for which this adapter is configured. The adapter gasket 604 is disposed over the volute nozzle 609 of the bodies 601 and 602.

Figure 47A:
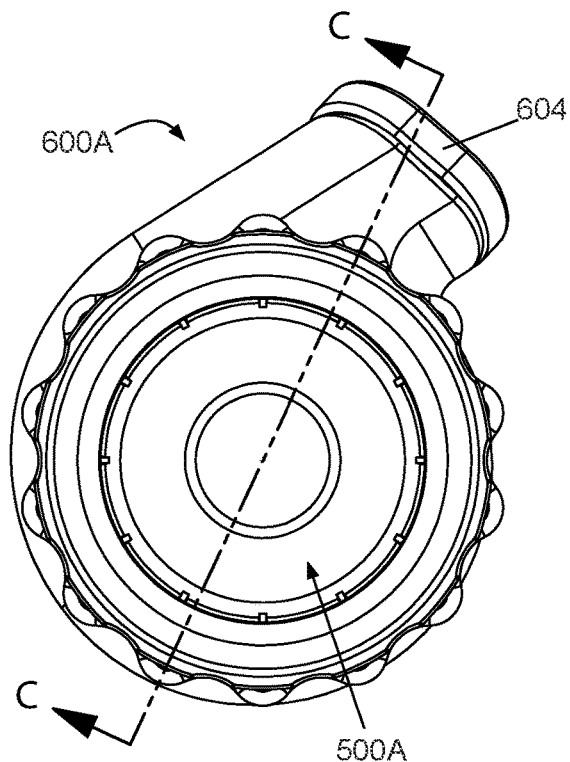
FIG. 47a is a top view of the threaded intake adapter assembly 600A of FIG. 45 and Section Line C, in accordance with an embodiment.
Figure 47B:
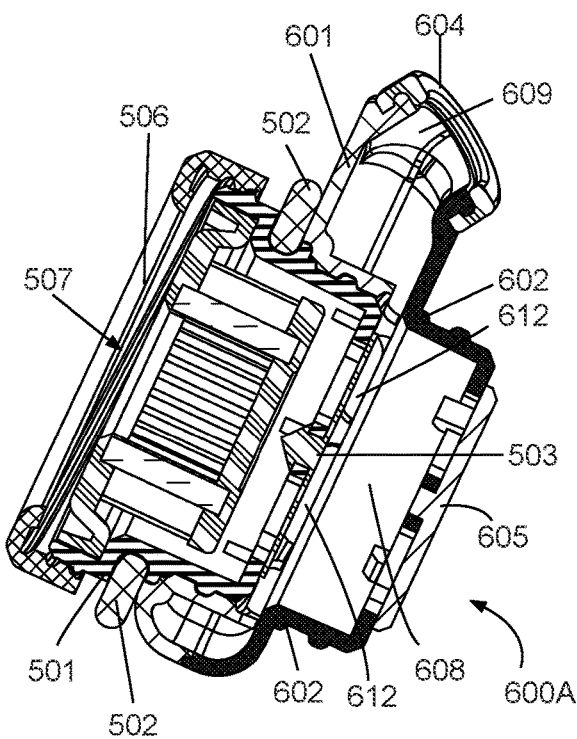
FIG. 47b shows a cross-sectional view of the threaded intake adapter assembly 600A along Section Line C, in accordance with an embodiment.
Figure 48A:
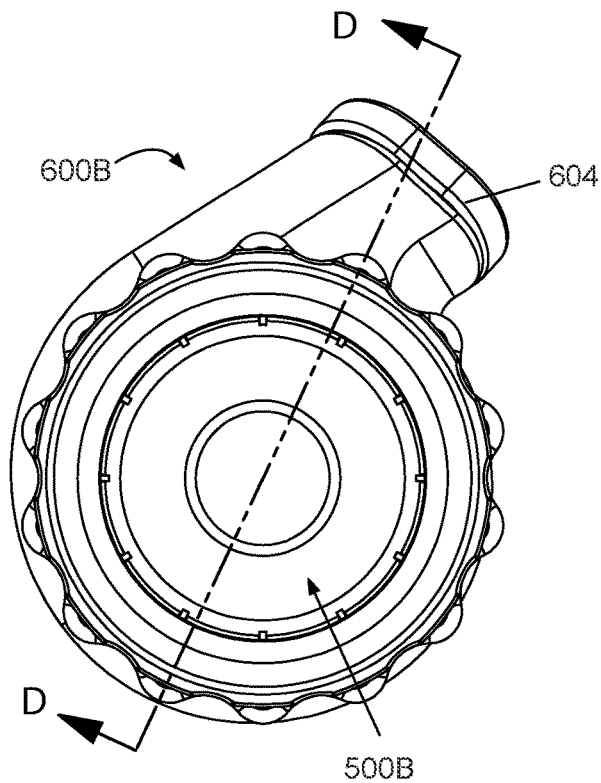
FIG. 48a is a top view of the threaded exhaust adapter assembly 600B of FIG. 46 and Section Line D, in accordance with an embodiment.
Figure 48B:
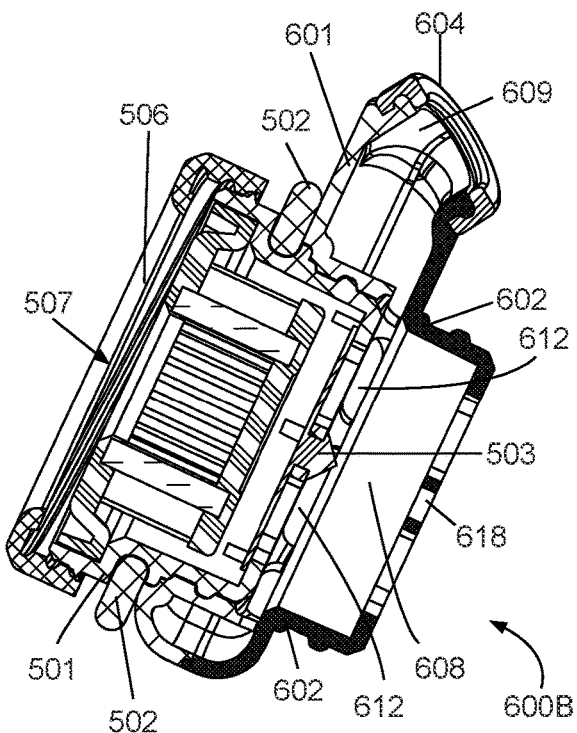
FIG. 48b shows a cross-sectional view of the threaded exhaust adapter assembly 600B along Section Line D, in accordance with an embodiment.

The Sections C and D of FIGS. 47b and 48b (established by FIGS. 47a and 48a respectively) show the placement and distances involved with the threaded adapter assemblies and the filter cartridges. The filter cartridges 500A/500B are inserted up to their grip ring 502, but there is still sufficient distance and volume for air to pass through the filter element 507 and through the vents 612 of the cartridge-side body 601. Because of the check valves 503 inside the filter cartridges 500A/500B, the threaded intake adapter assembly 600A and threaded exhaust adapter assembly 600B do not require check valves themselves. However, the intake adapter 600A comprises flow restrictor 605 to divert air through the vents 612 and through the collector region 610 to the volute nozzle 609. The inclusion and omission of a flow restrictor 605 in the various adapter assemblies 600A/600B is further shown in FIGS. 61a-61e.

Figure 49:
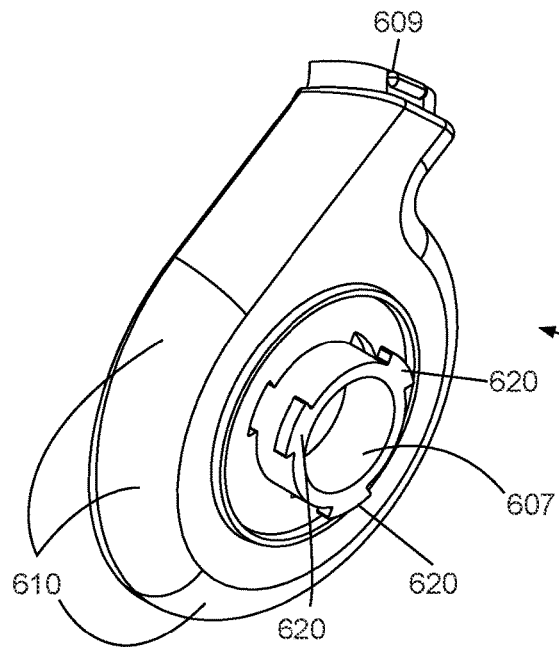
FIGS. 49 and 50 show the cartridge side housing 601 of the adapter assembly 600 in bayonet fitting configuration in a front and rear perspective view, respectively, in accordance with an embodiment.
Figure 50:
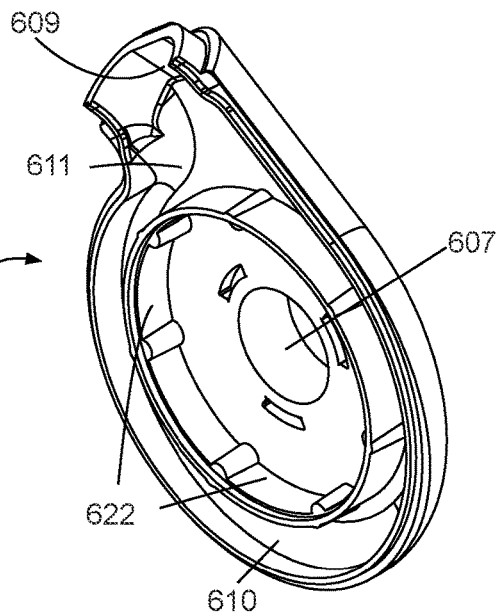
Figure 51:
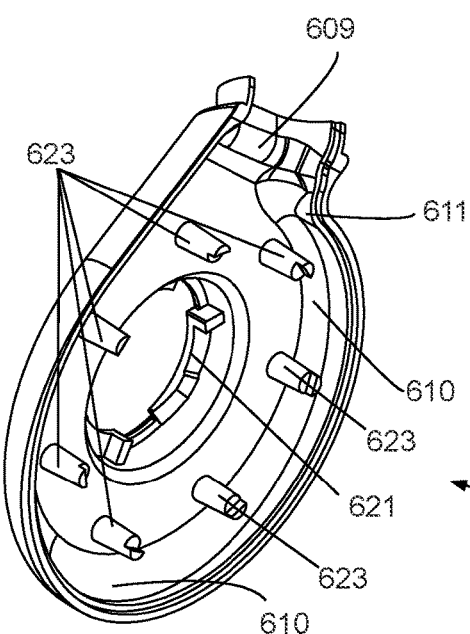
FIGS. 51 and 52 show the respirator side housing 602 of the adapter assembly 600 in bayonet fitting configuration in a front and rear perspective view, respectively, in accordance with an embodiment.
Figure 52:
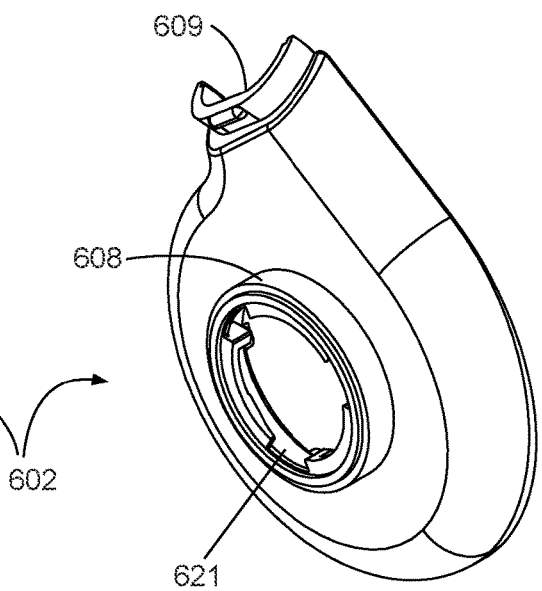

FIGS. 49 through 52 have the housings 601 and 602 utilizing bayonet fastener features according to another embodiment of the present disclosure. FIGS. 49 and 50 illustrate the cartridge-side body 601 in a front and rear perspective view, respectively, while FIGS. 51 and 52 show the respirator-side body 602 in a similar front and rear perspective view, respectively. The cartridge-side port 607 may be of different dimensions to the threaded variant, as this allows for male bayonet attachment points 620 to be integrated to the cartridge-side body 601. Internally, a sealing ring 622 is added to help direct the flow of air through the cartridge-side port 607 into the collector regions 610 of the assembly. On the respirator-side body 602, the respirator-side port 608 may comprise internal bayonet fittings 621 and support bosses 623. The respirator-side port 608 may be configured to seal with at least one of an intubation tube, an air hose, or an ambu bag.

Figure 53:
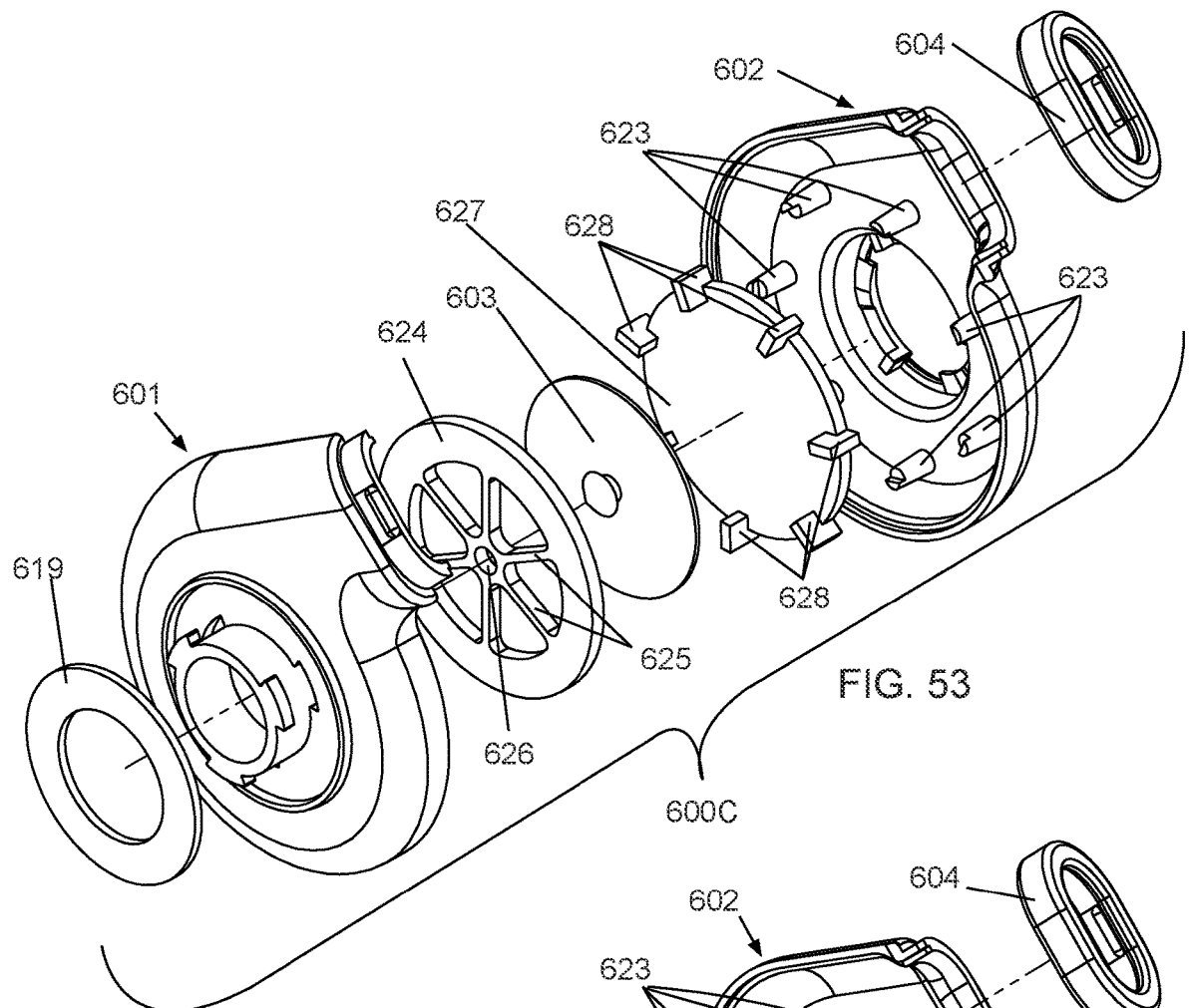
FIG. 53 is an exploded view of a bayonet fitted intake adapter assembly 600C, in accordance with an embodiment.
Figure 54:
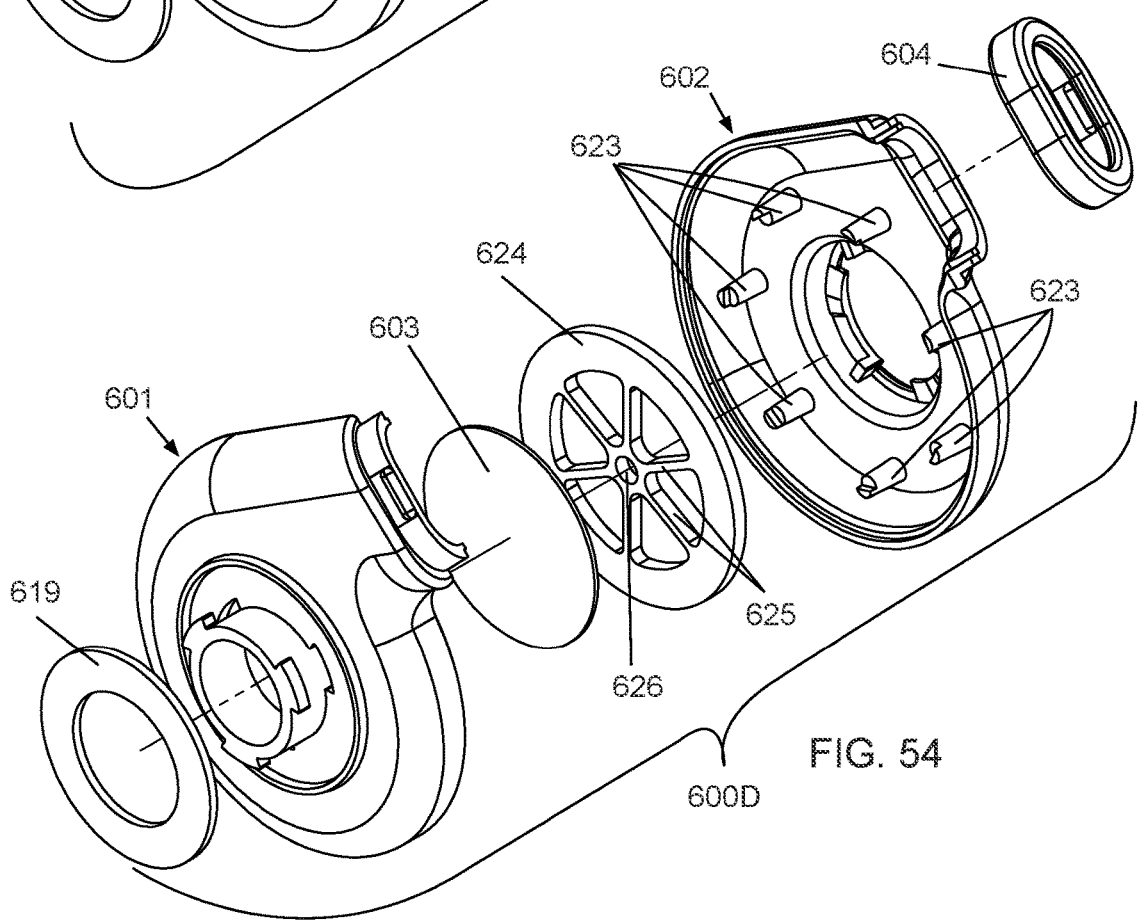
FIG. 54 is an exploded view of a bayonet fitted exhaust adapter assembly 600D, in accordance with an embodiment.
Figure 55A:
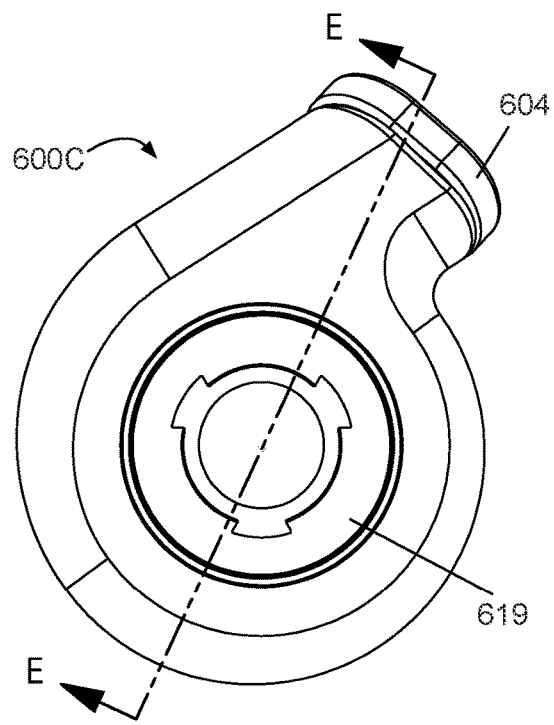
FIG. 55a is a top view of the bayonet fitted intake adapter assembly 600C of FIG. 53 and Section Line E, in accordance with an embodiment.
Figure 55B:
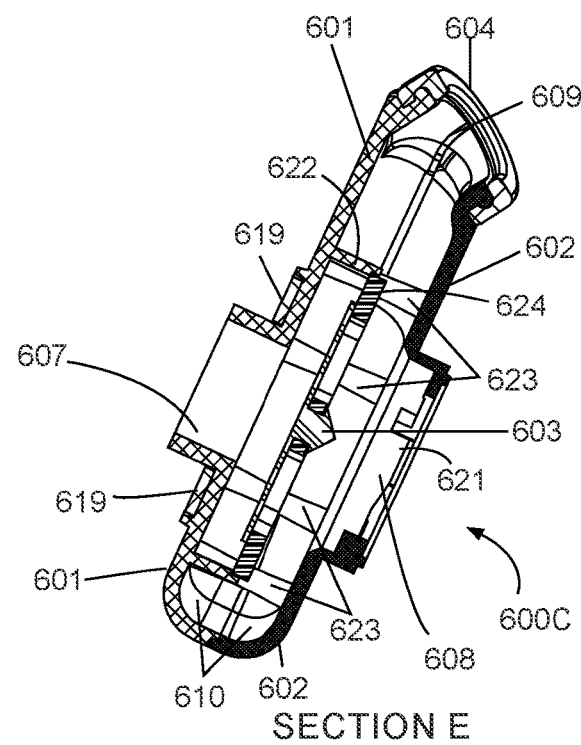
FIG. 55b shows a cross-sectional view of the bayonet fitted intake adapter assembly 600C of FIG. 53 along Section Line E, in accordance with an embodiment.
Figure 56A:
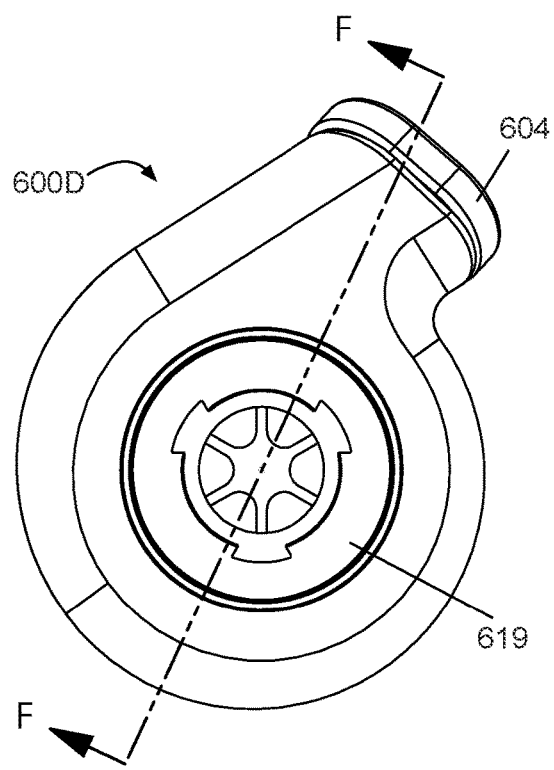
FIG. 56a is a top view of the bayonet fitted exhaust adapter assembly 600D of FIG. 54 and Section Line F, in accordance with an embodiment.
Figure 56B:
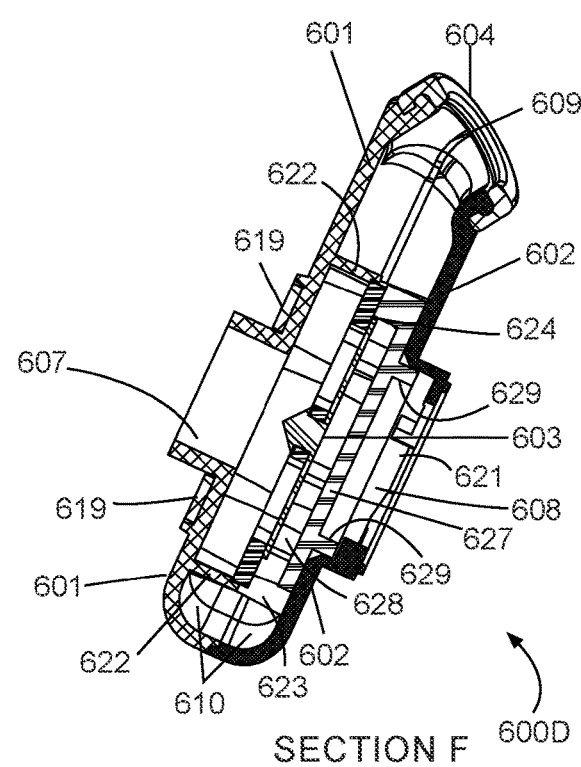
FIG. 56b shows a cross-sectional view of the bayonet fitted exhaust adapter assembly 600D of FIG. 54 along Section Line F, in accordance with an embodiment.

The exploded views of FIGS. 53 and 54, as well as the section views seen and established by FIGS. 55a-56b illustrate the configuration and importance of these features. The intake bayonet adapter assembly 600C features a gasket 619, a check valve insert 624 with an internally oriented check valve 603, and a flow restrictor 627. The gasket 619 is used for sealing the undercuts of the bayonet fittings 620 on the cartridge-side body 601, while the check-valve insert 624 with its open vent structure 625 and check valve port 626 makes the integration of a check valve 603 more manufacturing- and servicing-friendly. The support bases 623 and structural bosses 628 of the flow restrictor 627 on the respirator-side body 602 and the sealing ring 622 press against the check valve insert 624 to create a seal, with the check valve 603 regulating uni-directional flow of air. Particular to the Sections E and F of FIGS. 55b and 56b respectively, the support bosses 623 and structural bosses of the second embodiment flow restrictor 628 take the place of the vents 612 and stand-offs 614 found in FIGS. 39-48b. To help ensure a positive seal, the flow restrictor 628 comprises a sealing boss 629 on the side opposite its structural bosses 628.

Figure 57:
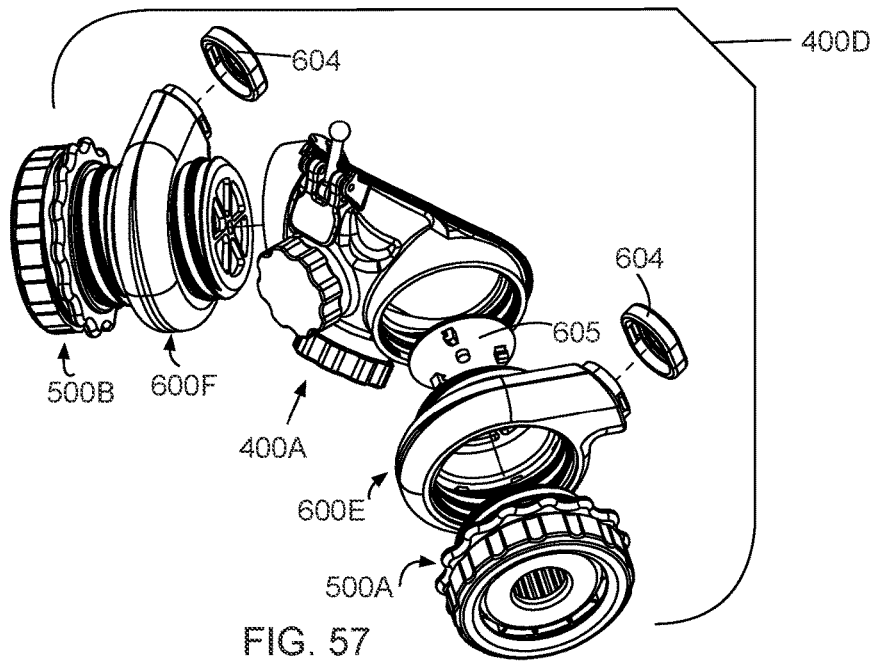
FIG. 57 is an exploded view of the adapted cartridge facepiece assembly 400D, illustrating one configuration of adapter installation in accordance with an embodiment.
Figure 58:
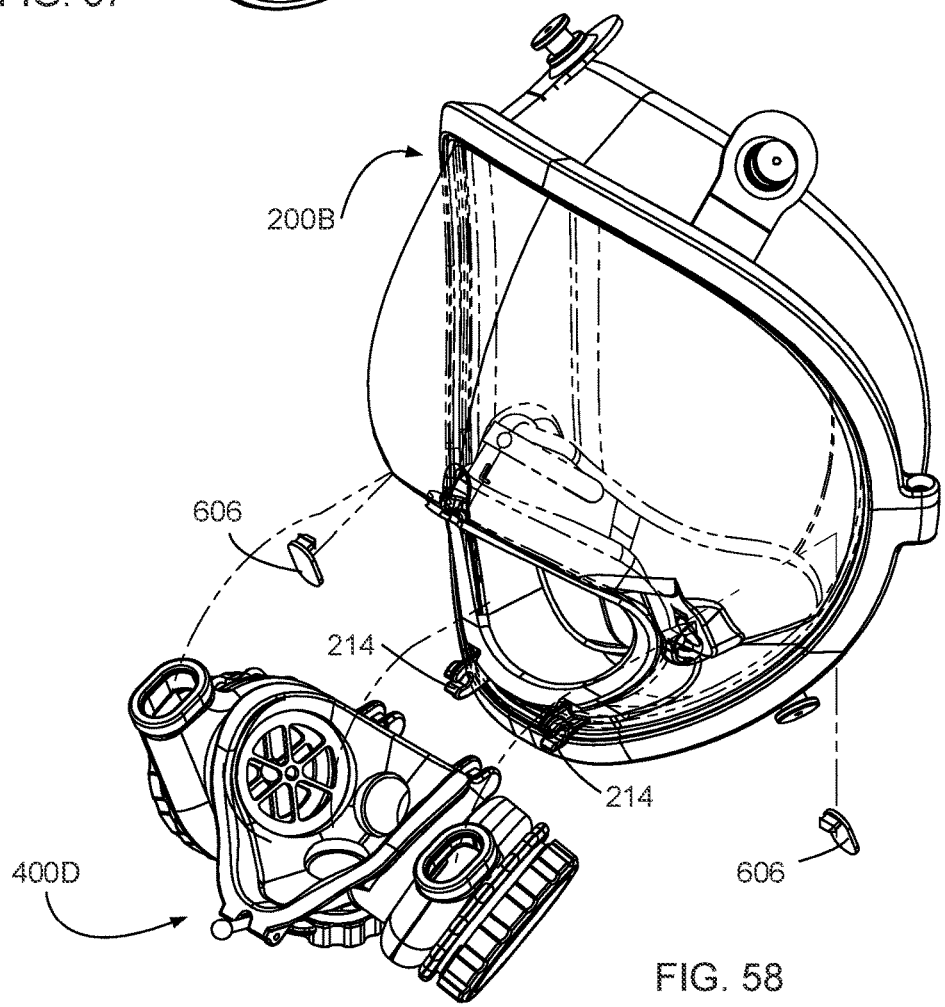
FIG. 58 is a perspective view of the full-face assembly 200B and adapted cartridge facepiece assembly 400D, specifically to illustrate the placement of anti-fog check valves 606 in accordance with one embodiment.

Turning to the adapter 600, the adapter 600 is used to direct the flow of air through the interior gas spaces of the full-face respirator 100B. According to one preferred embodiment, a left handed adapter assembly 600E is paired with the intake filter cartridge 500A, the flow restrictor 605, and an adapter gasket 604, while a right-handed adapter assembly 600F may be paired only with the exhaust filter cartridge 500B and the adapter gasket 604 of its own. When attached to a cartridge facepiece assembly 400A, the collection becomes an adapted cartridge facepiece assembly 400D, as seen in FIG. 57. In FIG. 58, the anti-fog check valves 606 are inserted into their ports on the full-face assembly 200B, at which point the adapted cartridge facepiece assembly 400D can be installed into the annular hinge knuckles 214 of the full-face lens 202, rotated into position and the keeper locking mechanism (i.e., the keeper bar 404 and the over center latch 405) engaged to seal the assembly.

FIGS. 59a-60c illustrate the installation of the anti-fog check valves 606 onto the full-face lens 202. As previously discussed, the full-face lens 202 has the oronasal opening 203, annular hinge knuckles 214, oronasal mounting stem port 211 for an oronasal mounting stem 210 (shown in, for example, FIG. 17), and keeper notch 215 of the half-face frame body 201. Present in these views are face seal alignment notches 223, located at the top and bottom of the full-face lens 202 to help orientate the face seal 216 during setup. On the inside of the lens 202 are oronasal mask support ribs 205 that help maintain the shape of the oronasal mask 206 in both half-face 100A and full-face 100B configurations. The Detail C of FIGS. 59b and 59c (established by FIG. 59a) show an anti-fog aperture 221, an anti-fog check valve port 222, and the outer adapter mating surface 225. Also visible is an oronasal mounting stem port 210 for the oronasal mounting stem 210. To configure an anti-fog aperture 221 as an exhaust port, the anti-fog check valve 606 must be inserted into its port 222 on the outer adapter mating surface 225 of the full-face lens 202, as shown in Detail C of FIGS. 60b and 60c. This means the anti-fog check valve 606 will open away from the full-face lens 202 into the volute nozzle of an adapter assembly 600. To configure an anti-fog aperture 221 as an intake port, the anti-fog check valve 606 must be inserted into the port 222 on an inner adapter mating surface 226 of the full-face lens 202 so that it opens into the interior lens space of the mask, as shown in Detail D of FIGS. 60a and 60b.

Lastly, FIGS. 61a-61e show the flow of air through the full-face respirator 100B. For clarity, the securing headgear 300B have been omitted from these illustrations.

Figure 61A:
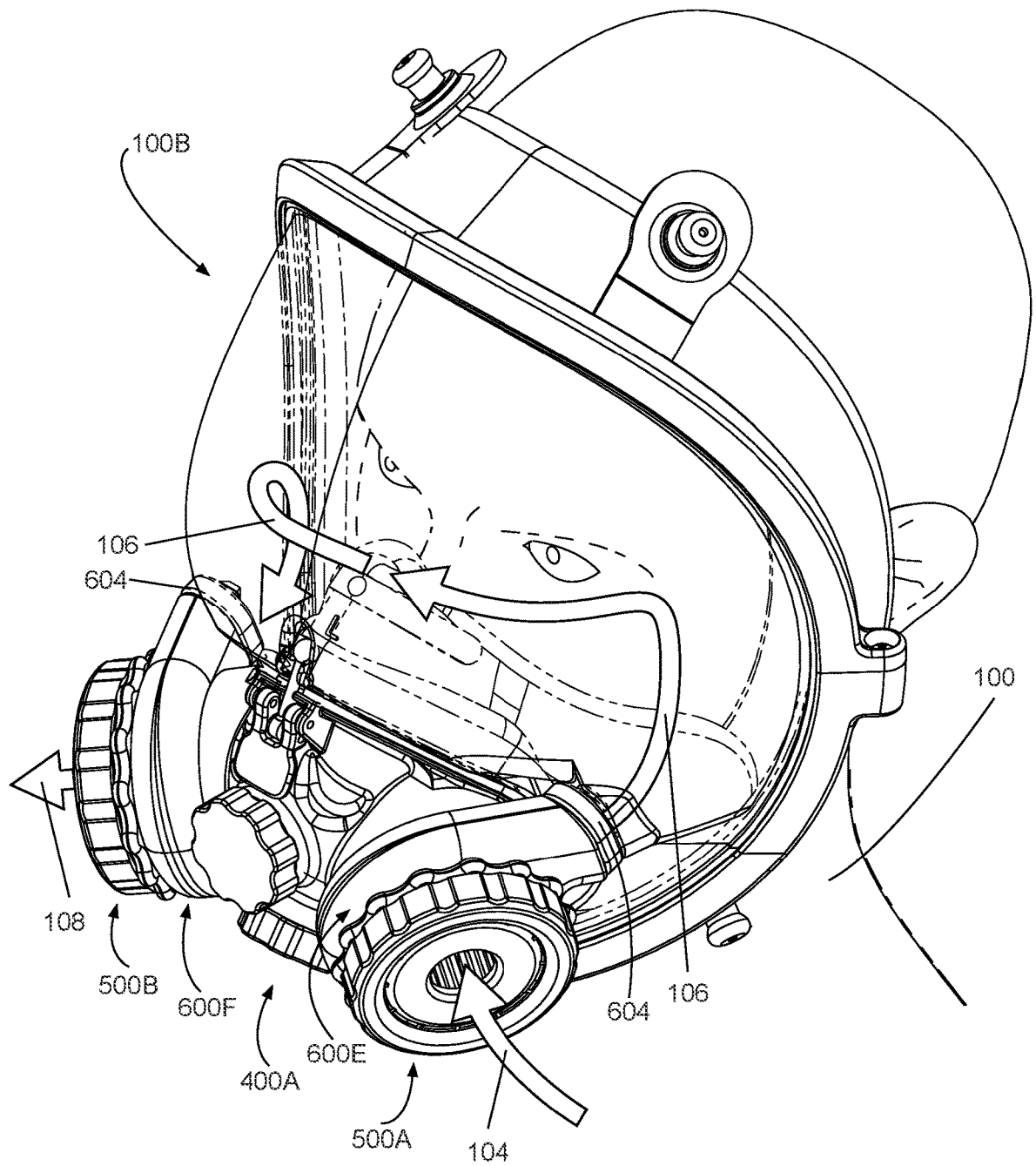

The perspective view of FIG. 61a and the Detail E and F of FIGS. 61d and 61e illustrate the overall flow of air through the full-face respirator 100B. Ambient air 104 from the environment is pulled into the intake filter cartridge 500A of the adapted cartridge facepiece assembly 400B (FIGS. 61a and 61e). This air 104 is pulled through the filter material 510, becoming cleaned air 105 that passes into the volute collecting regions 610 of the left hand adapter assembly 600E to the intake positioned anti-fog check valve 606 (FIG. 61e). In embodiments having the check valve 503 inside the intake filter cartridge 500A, it is not possible for the air 104 to backwash out of the respirator. The cleaned air 105 passes through the anti-fog aperture 221 into the interior lens space 103 of the respirator, where it passes by the face of the wearer 101 to the exhaust configured anti-fog port 606 (FIG. 61a). The interior lens space air 106 then enters the right-hand adapter assembly 600F, where it can then pass through the adapter to the interior mask space 102 of the respirator (FIG. 61d). This clean air 107 entering the mask is then inhaled by the wearer, saturated with carbon dioxide, and exhaled. Referring to the exhaust-configured anti-fog check valve 606 and an exhaust filter cartridge 500B with its own check valve 503, this exhaled air 108 exits through the exhaust filter cartridge 500B to be filtered by the filter material 510 of that cartridge before exiting out into the ambient air.

Alongside the benefits of the present disclosure that have been previously described, the additional advantages of the anti-fog air routing and adapter assemblies described above are numerous. Firstly, the oronasal mask 206 of the present disclosure may be used in either half-face or full-face configurations, as there are no extraneous holes or ports that need to be sealed other than those already sealed by the facepiece assemblies. To clarify, this means that at no point does the flow of air pass between the interior lens space 103 to the interior mask space 102 via openings or valves in the oronasal mask 206: it must instead be routed through the interior lens space 103 by way of the adapter assemblies 600E and 600F to the facepiece assembly 400A-400D and through the oronasal opening 203. Secondly, this means that the full-face respirator of the present disclosure benefits from the anti-fog and humidity control features common of the prior art respirators. Finally, because of the various check valves throughout the system, and the filtering elements at both the intake and exhaust ends, this means that cleaned air is filtered and continuously passes through the face lens into the interior gas space to be breathed, with little residue from the previously exhaled breath remaining. Further, because of the check valves and filter elements, this means the present respirators 100A/100B can pass filtered exhaled air into the ambient environment, thus reducing the chance of cross-contamination or infection in health care or emergency settings.

The above description of preferred embodiments should not be interpreted in a limiting manner since other variations, modifications and refinements are possible within the spirit and scope of the present disclosure. The scope of the invention(s) is defined in the appended claims and their equivalents.

What is claimed is:

1. A respirator for supplying clean air for a wearer, comprising:
    a face assembly comprising an oronasal mask configured to seal against and cover a nose region and a mouth region of the wearer;
    a securing headgear releasably securable with the face assembly, the securing headgear configured to secure the respirator on a head of the wearer; and
    a facepiece assembly for supplying the wearer with air for inhaling and releasing air exhaled by the wearer, the facepiece assembly releasably securable with the face assembly via an over center latch and a keeper bar.

2. The respirator of claim 1, wherein the face assembly comprises harness attachment elements, and wherein the securing headgear comprises one or more removable buckles configured to releasably and securely lock with the harness attachment elements.

3. The respirator of claim 1, wherein the securing headgear is adjustable.

4. The respirator of claim 1, wherein the face assembly comprises a half-face assembly configured to create a seal against and cover at least the nose region and the mouth region of the wearer.

5. The respirator of claim 1, wherein the face assembly comprises a full-face assembly configured to create a seal against the nose region, the mouth region, and an eye region of the wearer and cover at least a nose, a mouth, and eyes of the wearer.

6. The respirator of claim 5, further comprising lens releasably securable with the face assembly, the lens configured to cover at least the eyes of the wearer when engaged with the face assembly.

7. The respirator of claim 1, wherein the face assembly is interchangeable on the respirator between a half-face assembly and a full-face assembly.

8. The respirator of claim 1, wherein the facepiece assembly is interchangeable on the face assembly between a cartridge facepiece assembly, a negative-pressure filter facepiece assembly, a ventilator-adaptive facepiece assembly, and an adaptable cartridge facepiece assembly.

9. The respirator of claim 8, wherein the cartridge facepiece assembly is configured to releasably secure with one or more filter cartridges for filtering air.

10. The respirator of claim 8, wherein the negative-pressure filter facepiece assembly comprises a non-cartridge facepiece body, a breathing port, and a filter element secured by the non-cartridge facepiece body disposed between the breathing port and the wearer.

11. The respirator of claim 1, wherein one or more of the face assembly, the facepiece assembly, or the securing headgear are configured to be released from the respirator, sterilized, and releasably resecured with the respirator.

12. A respirator for filtering air for a wearer, comprising:
    a full-face assembly configured to create a seal against a mouth region, a nose region, and an eye region and cover at least a mouth, a nose, and eyes of the wearer, the full-face assembly including:
        an interior gas space defined by the seal of the full-face assembly,
        lens releasably securable with the full-face assembly, the lens configured to cover at least the eyes of the wearer when engaged with the full-face assembly, and
        an oronasal mask configured to cover the nose and the mouth of the wearer, the oronasal mask releasably securable with the full-face assembly; and
    an adaptable cartridge facepiece assembly releasably securable with the full-face assembly including:
        a cartridge facepiece body, and
        adapters configured to direct airflow into the interior gas space through an intake filter cartridge and out of the interior gas space through an exhaust filter cartridge,
        wherein the adaptable cartridge facepiece assembly and the full-face assembly are releasably securable via a keeper bar and an over center latch.

13. The respirator of claim 12, further comprising anti-fog check valves configured to direct airflow into, through, and out of the interior gas space.

14. The respirator of claim 12, wherein the intake filter cartridge and the exhaust filter cartridge are releasably secured with the adaptable cartridge facepiece assembly, and the adapters is disposed and in gaseous communication between the cartridge facepiece body, the intake filter cartridge, and the exhaust filter cartridge.

15. The respirator of claim 12, wherein one or more of the full-face assembly, the adaptable cartridge facepiece assembly, or the adapters are configured to be released from the respirator, sterilized, and releasably resecured with the respirator.

16. A respirator for supplying clean air for a wearer in need of assisted breathing, comprising:
    a face assembly defining an interior gas space, the face assembly including a mask configured to seal against and cover at least a nose region and a mouth region of the wearer; and
    a facepiece assembly for supplying the wearer with air for inhaling and releasing air exhaled by the wearer, the facepiece assembly releasably securable with the face assembly mask and interchangeable on the respirator between two or more of a cartridge facepiece assembly, a negative-pressure filter facepiece assembly, a ventilator-adaptive facepiece assembly, and an adaptable cartridge facepiece assembly, wherein
    the facepiece assembly is releasably securable with the face assembly via an over center latch and a keeper bar.

17. The respirator of claim 16, wherein the facepiece assembly comprises the ventilator-adaptive facepiece assembly, wherein the ventilator-adaptive facepiece assembly includes a port configured to be in gaseous communication with the interior gas space, and wherein the port is configured to seal with the at least one of an intubation tube, an air hose, or an ambu bag.

18. The respirator of claim 16, wherein one or more of the face assembly and the facepiece assembly are configured to be released from the respirator, sterilized, and releasably resecured with the respirator.

* * * * *